(12) United States Patent
Andreotti et al.

(10) Patent No.: US 6,900,183 B2
(45) Date of Patent: May 31, 2005

(54) MACROLIDE ANTIBIOTICS

(75) Inventors: Daniele Andreotti, Verona (IT); Stefano Biondi, Verona (IT); Sergio Lociuro, Verona (IT)

(73) Assignee: Glaxo Group Limited, Greenford (GB)

( * ) Notice: Subject to any disclaimer, the term of this patent is extended or adjusted under 35 U.S.C. 154(b) by 0 days.

(21) Appl. No.: 10/450,886

(22) PCT Filed: Dec. 20, 2001

(86) PCT No.: PCT/GB01/05669

§ 371 (c)(1),
(2), (4) Date: Dec. 3, 2003

(87) PCT Pub. No.: WO02/50092

PCT Pub. Date: Jun. 27, 2002

(65) Prior Publication Data

US 2004/0082526 A1 Apr. 29, 2004

(30) Foreign Application Priority Data

Dec. 21, 2000 (GB) .............................................. 0031312

(51) Int. Cl.⁷ .......................... A61K 31/70; C07H 17/08
(52) U.S. Cl. ........................... 514/29; 536/7.2; 536/7.3; 536/7.4
(58) Field of Search ............................ 514/29; 536/7.2, 536/7.3, 7.4

(56) References Cited

U.S. PATENT DOCUMENTS 6,011,142 A 1/2000 Chappert et al.
6,124,269 A 9/2000 Phan et al.

FOREIGN PATENT DOCUMENTS

EP 1 114 826 A 11/2001
WO WO 00/55168 9/2000

*Primary Examiner*—Elli Peselev
(74) *Attorney, Agent, or Firm*—Laura K. Madden; Loretta J. Henderson; Mary E. McCarthy

(57) ABSTRACT

11,12 γ lactone ketolides of the following formula:

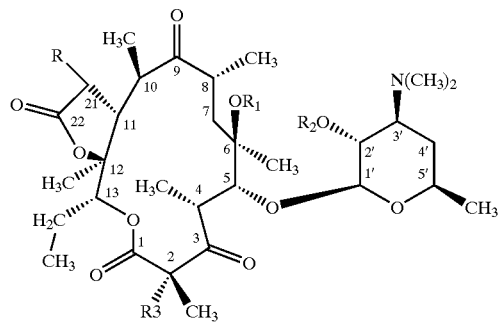

and pharmaceutically acceptable salts and solvates thereof, wherein R, $R_1$, $R_2$, and $R_3$ are as described herein. The disclosure also relates to processes for the preparation of such compounds, to compositions containing them, and to their use in the therapy or prophylaxis of systemic or topical bacterial infections in a human or animal body.

9 Claims, No Drawings

MACROLIDE ANTIBIOTICS

CROSS REFERENCES TO RELATED APPLICATIONS

This application is a National Stage Application filed under 35 U.S.C.§371 of PCT/GB01/05669, filed on Dec. 20, 2001, which claims priority of GB Application No. GB0031312.2, filed Dec. 21, 2000.

The present invention relates to novel semi-synthetic macrolides having antibacterial activity. More particularly this invention relates to 11,12 γ lactone ketolides, to processes for their preparation, to compositions containing them and to their use in medicine.

EP 1114826 inter alia generically discloses macrolide compounds of formula (A) having antibacterial activity

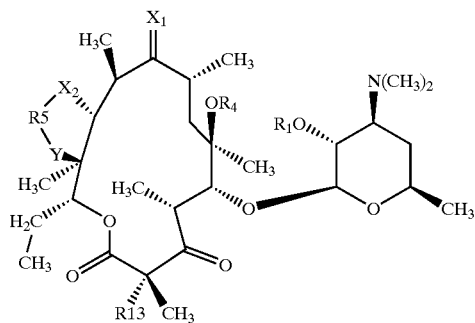

(A)

wherein $R_1$ is hydrogen or a hydroxyl protecting group; $R_4$ is inter alia an optionally substituted $C_{1-10}$ alkyl, $X_1$ is inter alia oxygen, $X_2$ is inter alia $CH_2$, Y is NH, O or S, $R_5$ is inter alia C(O) and $R_{13}$ is hydrogen or halo.

We have now found novel 11,12 γ lactone ketolides having antibacterial activity.

Thus, the present invention provides compounds of general formula (I)

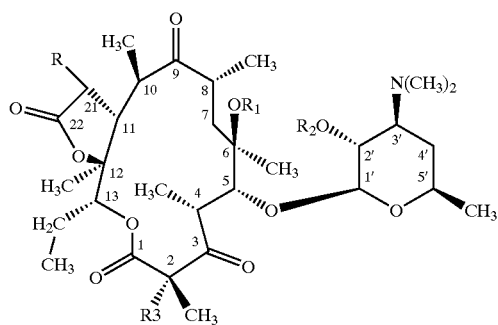

(I)

wherein
R is hydrogen, cyano or $NR_4R_5$;
$R_1$ is $XR_6$;
$R_2$ is hydrogen or a hydroxyl protecting group;
$R_3$ is hydrogen or halogen;
$R_6$ is selected from:
 optionally substituted phenyl;
 optionally substituted 5 or 6 membered heteroaryl in which the 5-membered heteroaryl contains at least one heteroatom selected from oxygen, sulphur or nitrogen and the 6-membered heteroaryl group contains from 1 to 3 nitrogen atoms, optionally substituted 5–6 membered heterocyclic,
optionally substituted 9 to 10 membered fused bicyclic carbocyclic; or
$R_6$ is an optionally substituted 9 or 10 membered fused bicyclic heterocyclic having at least one heteroatom selected from oxygen, sulphur or nitrogen;
X is a $C_{1-10}$ alkylene, a $C_{3-10}$ alkenylene or a $C_{3-10}$ alkynylene chain wherein said chains are:
 i) optionally interrupted by a bivalent radical group selected from —N($R_5$)—, —C(O)—, —S(O)n—, —N($R_5$)C(O)—, —C(O)N($R_5$)—,
 ii) optionally substituted by one or two groups selected from:
  $C_{1-4}$ alkyl, oxo, $C_{1-4}$ alkoxy, halogen, cyano, phenoxy, hydroxy, $NR_4R_5$;
$R_4$ is hydrogen, $C_{1-4}$ alkyl or C(O)$R_5$;
$R_5$ is hydrogen or $C_{1-4}$ alkyl;
n is 0 or an integer from 1 to 2;
and pharmaceutically acceptable salts and solvates thereof.

A further embodiment of the invention provides compounds of general formula (I) wherein
R is hydrogen, cyano or $NR_4R_5$;
$R_1$ is $XR_6$;
$R_2$ is hydrogen or a hydroxyl protecting group;
$R_3$ is hydrogen or halogen;
$R_6$ is selected from:
 optionally substituted phenyl;
 optionally substituted 9 to 10 membered aromatic fused bicyclic carbocyclic ring;
 optionally substituted 5 or 6 membered heteroaryl in which the 5-membered heteroaryl contains at least one heteroatom selected from oxygen, sulphur or nitrogen and the 6-membered heteroaryl group contains from 1 to 3 nitrogen atoms;
 $R_6$ is optionally substituted fused bicyclic heteroaryl groups containing 9 or 10 ring members having at least one heteroatom selected from oxygen, sulphur or nitrogen;
X is a group selected from:
 $C_{1-6}$ alkyl, optionally substituted by one or two groups selected from a $C_{1-4}$ alkoxy, hydroxy or by $NR_4R_5$;
 $C_{3-6}$ alkenyl group optionally substituted by one or two groups selected from $C_{1-4}$ alkoxy, a halogen, a hydroxy or by a $NR_4R_5$ group;
 $C_{3-6}$ alkynyl;
 $(CH_2)pY(CH_2)q$ wherein Y is selected from CO, S(O)n, $NR_5$, $N(R_5)C(O)$ or $C(O)N(R_5)$;
$R_4$ is hydrogen, $C_{1-4}$ alkyl or C(O)$R_5$;
$R_5$ is hydrogen or $C_{1-4}$ alkyl;
p is 0 or an integer from 1 to 4; q is 0 or an integer from 1 to 5; with the proviso that the sum of p and q is an integer from 0 to 5; n is 0 or an integer from 1 to 2; provided that when Y is $NR_6$, S(O)n or $N(R_5)C(O)$, p is not 0 or 1; and pharmaceutically acceptable salts and solvates thereof.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, fumarates and maleates.

The compound of formula (I) and salts thereof may form solvates and the invention includes all such solvates. The solvates may, for example, be hydrates.

References hereinafter to a compound according to the invention include both compounds of formula (I) and their pharmaceutically acceptable acid addition salts together with pharmaceutically acceptable solvates.

The compound of formula (I) and salts thereof may form solvates (e.g. hydrates) and the invention includes all such solvates.

In the general formula (I) as drawn, the solid wedge shaped bond indicates that the bond is above the plane of the paper. The broken bond indicates that the bond is below the plane of the paper.

It will be appreciated by those skilled in the art that the compounds of formula (I) when R is not hydrogen contain further one chiral centre (namely the carbon atom shown as 21 in formula (I)) and this may be represented by the formulae (1a) and (1b).

The configuration for the carbon atom shown as 21 in formula 1a is hereinafter referred to as the β configuration and in formula 1b as the α configuration.

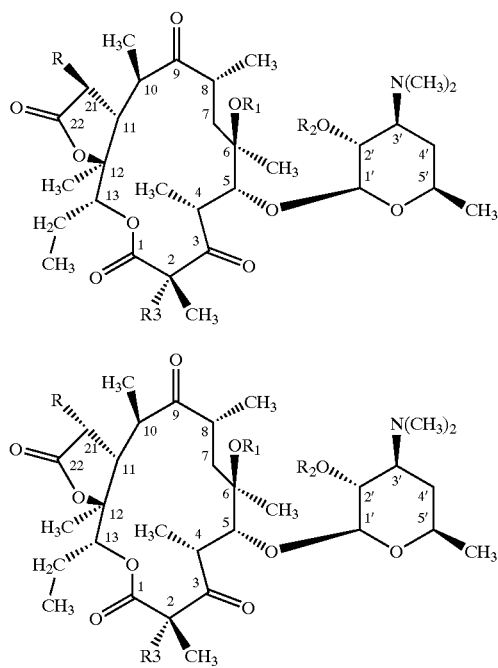

It is to be understood that the two diastereoisomers (1a, 1b) and mixtures thereof are encompassed within the scope of the present invention.

Compounds wherein $R_2$ represents a hydroxyl protecting group are in general intermediates for the preparation of other compounds of formula (I).

Compounds wherein $R_2$ represents a hydroxyl protecting group are in general intermediates for the preparation of other compounds of formula (I).

When the group $OR_2$ is a protected hydroxyl group this is a non-toxic protecting group, conveniently $OR_2$ is an acyloxy group (i.e. acetoxy or benzyloxy).

The term $C_{1-4}$ alkyl as used herein as a group or a part of the group refers to a straight or branched alkyl group containing from 1 to 4 carbon atoms; examples of such groups include methyl, ethyl, propyl, isopropyl, n-butyl, isobutyl and tert-butyl.

The term $C_{1-10}$ alkylene chain refers to straight or branched chain containing from 1 to 10 carbon atoms examples of such group include, but are not limited to methylene, ethylene, propylene, isopropylene, n-butylene, isobutylene, tert-butylene, pentylene, n-heptylene, n-octylene, n-nonylene and n-decylene.

The term $C_{3-10}$ alkenylene chain refers to a straight or branched alkylene chain containing from 3 to 12 carbon atoms and having at least one double bond; examples of such groups include 2-propenylene, 1-propenylene, isopropenylene, 2-butenylene, 2-pentenylene, 2-hexenylene and the like.

The term $C_{3-10}$ alkynylene chain refers to a straight or branched alkylene chain containing from 3 to 12 carbon atoms and having at least one triple bond; examples of such groups include 2-propynylene, 1-propynylene, isopropynylene, 2-butynylene, 2-pentynylene, 2-hexynylene and the like.

The term halogen refers to a fluorine, chlorine, bromine or iodine atom.

Examples of 5 or 6 membered heteroaryl group according to the invention include furanyl, thiophenyl, pyrrolyl, imidazolyl, thiazolyl, oxazolyl, pyrazolyl, isoxazolyl, isothiazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2, 5-triazinyl or 1,3,5-triazinyl and the like.

The term 9 to 10 membered fused bicyclic heterocyclic group refers to a 5,6/6,5 or 6,6 bicyclic ring system, containing at least one heteroatom selected from oxygen, sulphur or nitrogen, which may be saturated, unsaturated or aromatic. The term 9 to 10 membered fused bicyclic heterocyclic group also refers to a phenyl fused to one 5 or 6 membered heterocyclic group. Example of such groups include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3 benzo[1,3]dioxolyl, 2H-chromanyl, isochromanyl, 5-oxo-2,3 dihydro-5H-[1,3]thiazolo[3,2-a] pyrimidyl, 1,3-benzothiazolyl, 1,4,5,6 tetrahydropyridaziyl, 1,2,3,4,7,8 hexahydropteridinyl, 2-thioxo2,3,6,9-tetrahydro-1H-purin-8-yl, 3,7-dihydro-1H-purin-8-yl, 3,4 dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3 dihydro-1H-indolyl, 1,3-dihydro-2H-isoindol-2-yl, 2,4,7-trioxo-1,2,3,4,7,8-hexahydropteridinyl, thieno[3,2-d]pyrimidinyl, 4-oxo-4,7-dihydro-3H-pyrrolo[2,3-d]pyrimidinyl, 1,3 dimethyl-6-oxo-2-thioxo-2,3,6,9-tetrahydro-1H-purinyl, 1,2 dihydroisoquinolinyl, 2-oxo-1,3-benzoxazolyl, 2,3-dihydro-5H-1,3-thiazolo[3,2-a]pyrimidinyl, 5,6,7,8-tetrahydroquinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4 dihydropyrimidin-1-yl imidazolylpiridyl, quinoliyl, isoquinolinyl, quinazolinyl, quinoxalinyl, naphthyridinyl, pyrazolyl[3,4]pyridine, 1,2 di hydroisoquinolinyl, cinnolinyl, 2,3dihydro-benzo[1,4] dioxin-6-yl, 4,5,6,7-tetrahydro-benzo[b]thiophenyl-2-yl, 1,8naphthyridinyl, 1,6naphthyridinyl, 3,4dihydro-2H-1,4-benzothiazine, 4,8-Dihydroxy-quinolinyl, 1-oxo-1,2-dihydro-isoquinolinyl or 4-phenyl-[1,2,3]thiadiazolyl and the like.

The term 9 to 10 membered fused bicyclic carbocyclic group refers to a 5,6/6,5 or 6,6 bicyclic carbocyclic ring system which may be saturated, unsaturated or aromatic. It also refers to a phenyl fused to one 5 or 6 membered saturated or unsaturated carbocyclic group. Examples of such groups include naphthyl, 1,2,3,4 tetrahydronaphthyl, indenyl or indanyl and the like.

When $R_6$ is a substituted phenyl or a substituted 5 or 6 membered heteroaryl group this refers to a phenyl or a 5 or 6 membered heteroaryl group which is substituted by 1 to 2 groups, which may be the same or different, selected from $(CH_2)_rR_7$ group wherein r is zero or an integer from 1 to 4 and $R_7$ is selected from:
  hydrogen;
  halogen;
  $C_{1-4}$alkoxy;
  hydroxy;
  cyano;
  nitro;
  trifluoromethyl;
  carboxy;
  $NR_4R_5$;
  $CONR_4R_5$;
  $NHCOR_8$ wherein $R_8$ is $C_{1-4}$alkyl phenyl, 5 membered heteroaryl containing at least 1 heteroatom selected from oxygen, sulphur or nitrogen or 6-membered heteroaryl group containing at least 1 nitrogen atoms;
  $NR_5CONR_8R_5$;
  $NHS(O_2)R_9$ (wherein $R_9$ is $C_{1-4}$alkyl or phenyl);
  $S(O)_nR_8$ (wherein n is 0 or an integer from 1 to 2);
  $C_{1-4}$ alkanoyl amino;
  phenyl (optionally substituted by halogen, $C_{1-4}$alkoxy or $NR_4R_5$);
  phenoxy;
  5-membered heteroaryl containing at least 1 heteroatoms selected from oxygen, sulphur or nitrogen and a 6-membered heteroaryl group containing at least 1 nitrogen atom.

When $R_6$ is an optionally substituted 9 to 10 fused bicyclic heteroaryl group or substituted 9 to 10 membered fused bicyclic carbocyclic ring, such groups are optionally substituted by one to 2 substituents which may be the same or different and selected from alkyl, halogen, cyano, nitro, trifluoromethyl and $NR_4R_5$.

When X is a $C_{1-10}$ alkylene, a $C_{3-10}$ alkenylene or a $C_{3-10}$ alkynylene chain which is interrupted by a bivalent radical group selected from —$N(R_5)$—, —$C(O)$—, —$S(O)n$—, —$N(R_5)C(O)$—, —$C(O)N(R_5)$—, this refers for example to —$C_{1-10}$alkylene-$N(R_5)$—, $C_{1-10}$ alkylene-$C(O)$—, $C_{1-10}$alkylene-$S(O)n$—, $C_{1-10}$ alkylene-$N(R_5)C(O)$—, $C_{1-10}$ alkylene-$C(O)N(R_5)$—,$C_{3-10}$alkenylene-$N(R_5)$—,$C_{3-10}$ alkenylene-$C(O)$—, $C_{3-10}$ alkenylene-$S(O)n$—, $C_{3-10}$ alkenylene-$N(R_5)C(O)$—, $C_{3-10}$ alkenylene-$C(O)N(R_5)$—, $C_{3-10}$alkynylene-$N(R_5)$—, $C_{3-10}$alkynylene-$C(O)$—, $C_{3-10}$alkynylene-$S(O)n$—, $C_{3-10}$alkynylene-$N(R_5)C(O)$—, $C_{3-10}$ alkynylene-$C(O)N(R_5)$,
or this refers to a $C_{1-10}$ alkylene, a $C_{3-10}$ alkenylene or a $C_{3-10}$ alkynylene chain containing a bivalent radical group selected from:
—$N(R_5)$—, —$C(O)$—, —$S(O)n$—, —$N(R_5)C(O)$—, —$C(O)N(R_5)$—.

When X is an optionally substituted $C_{1-10}$ alkylene, $C_{3-10}$ alkenylene or $C_{3-10}$ alkynylene interrupted by a bivalent radical selected from —$N(R_5)$—, —$S(O)n$—, —$N(R_5)C(O)$— said bivalent radicals are preferably linked the oxygen atom by an optionally substituted alkylene chain containing at least two carbon atoms.

When X is an optionally substituted $C_{3-10}$ alkenylene, preferably this chain contains one double bond at the two terminal carbon atoms of the chain.

When X is an optionally substituted $C_{3-10}$ alkenylene which is interrupted by a bivalent radical group selected from —$N(R_5)$—, —$C(O)$—, —$S(O)n$—, —$N(R_5)C(O)$—, —$C(O)N(R_5)$—, said bivalent radicals are preferably linked to the double bond by an optionally substituted alkylene chain containing at least one carbon atom.

When X is an optionally substituted $C_{3-10}$ alkynylene, preferably this chain contains one triple bond at the two terminal carbon atoms of the chain.

When X is an optionally substituted $C_{3-10}$ alkynylene which is interrupted by a bivalent radical group selected from —$N(R_5)$—, —$C(O)$—, —$S(O)n$—, —$N(R_5)C(O)$—, —$C(O)N(R_5)$—, said bivalent radicals are preferably linked to the triple bond by an optionally substituted alkylene chain containing at least one carbon atom.

A preferred group of compounds of formula (I) are those in which the carbon atom shown as 21 is in the β configuration.

$R_2$ is preferably hydrogen.
$R_3$ is preferably hydrogen or fluorine.
$R_4$ and $R_5$ are preferably hydrogen.
$R_6$ is preferably phenyl, quinolinyl, pyridinyl-imidazolyl or pyridinyl-4-thiazolyl.
X is preferably a $C_{1-6}$ alkylene or $C_{3-6}$ alkenylene chain.

A preferred group of compounds of formula (I) is that wherein X is a $C_{1-6}$ alkylene or $C_{3-6}$ alkenylene chain, $R_6$ is a group selected from phenyl, quinolinyl, pyridyl-imidazolyl, pyridyl-4-thiazolyl and $R_2$, $R_3$, $R_4$ and $R_5$ are hydrogen.

Particularly preferred compounds of the invention are selected from:
(11S,21R)-3-Decladinosyl-11,12-dideoxy-6-O-[(quinolin-3-yl)-propen-3-yl]-3-oxo-12,11-[oxycarbonyl-(cyano)-methylene]-erythromycin A;
(11S)-3-Decladinosyl-11,12-dideoxy-6-O-[(quinolin-3-yl)-propen-3-yl]-3-oxo-12,11-[oxycarbonyl-methylene]-erythromycin A;
(11S,21R)-3-Decladinosyl-11,12-dideoxy-6-O-[(quinolin-5-yl)-propen-3-yl]-3-oxo-12,11-[oxycarbonyl-(cyano)-methylene]-erythromycin A;
(11S,21R)-3-Decladinosyl-11,12-dideoxy-6-O-[(quinolin-6-yl)-propen-3-yl]-3-oxo-12,11-[oxycarbonyl-(cyano)-methylene]-erythromycin A;
(11S,21R)-3-Decladinosyl-11,12-dideoxy-6-O-[(quinolin-7-yl)-propen-3-yl]-3-oxo-12,11-[oxycarbonyl-(cyano)-methylene]-erythromycin A;
(11S,21R)-3-decladinosyl-11,12-dideoxy-6-O-[(quinolin-5-yl)-propen-3-yl]-3-oxo-12,11-[oxycarbonyl-methylene]-erythromycin A;
(11S,21R)-3-decladinosyl-11,12-dideoxy-6-O-[(quinolin-6-yl)-propen-3-yl]-3-oxo-12,11-[oxycarbonyl-methylene]-erythromycin A.

Compounds according to the invention also exhibit a broad spectrum of antibacterial activity against a wide range of clinical pathogenic microorganisms.

For example, using a standard microtiter broth serial dilution test, compounds of the invention have been found to exhibit useful levels of activity against a wide range of pathogenic microorganisims including strains of *Staphylococcus aureus, Streptopococcus pneumoniae, Moraxella catarrhalis, Streptococcus pyogenes, Haemophilus influenzae.*

The compounds of the invention may therefore be used for treating a variety of diseases caused by pathogenic bacteria in human beings and animals.

Thus, according to another aspect of the present invention, we provide a compound of formula (I) or a physiologically acceptable salt thereof for use in the therapy in a human or animal subject.

According to a further aspect of the invention we provide the use of a compound of formula (I) or a physiologically acceptable salt thereof for the manufacture of a therapeutic agent for the treatment of systemic or topical bacterial infections in a human or animal body.

According to a yet further aspect of the invention we provide a method of treatment of the human or non-human animal body to combat bacterial infections which method comprises administering to the body an effective amount of a compound of formula (I) or a physiologically acceptable salt thereof.

The term treatment is also meant to include prophylaxis.

While it is possible that, for use in therapy, a compound of the invention may be administered as the raw chemical, it is preferable to present the active ingredient as a pharmaceutical formulation.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genito-urinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories, e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, e.g. dichlorodifluoromethane, trichlorofluoromethane, dichlorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01–99% of the active material. For topical administration, for example, the composition will generally contain from 0.01–10%, more preferably 0.01–1% of the active material.

For systemic administration the daily dose as employed for adult human treatment it will range from 2–100 mg/kg body weight, preferably 5–60 mg/kg body weight, which may be administered in 1 to 4 daily doses, for example, depending on the route of administration and the condition of the patient. When the composition comprises dosage units, each unit will preferably contain 200 mg to 1 g of active ingredient.

The duration of treatment will be dictated by the rate of response rather than by arbitrary numbers of days.

Compounds of general formula (I) and salts thereof may be prepared by general method outlined hereinafter. In the following description, the groups $R_1$, $R_2$, $R_3$, $R_4$, $R_5$, $R_6$, $R_7$, $R_8$, $R_9$, q or r and X have the meanings defined for the compounds of formula (I) unless otherwise stated.

Compounds of formula (I) in which R is hydrogen may be prepared by decarboxylation of a compound of formula (II), wherein $R_{1a}$ has the meaning defined above for formula (I) for $R_1$ or is a group convertible thereto, $R_{10}$ is a cladinose derivative of formula (III) or hydroxy, $R_{11}$ is hydrogen or $R_{11}$ together $R_{10}$ is an oxygen atom, followed if required, subjecting the resulting compound to one or more of the following operations: a) conversion of the group $R_{1a}$ into the group $R_1$; b) hydrolysis of the cladinose derivative (III); c) conversion of the 3-hydroxy group into the 3-oxo and d) removal of the protecting group $R_2$.

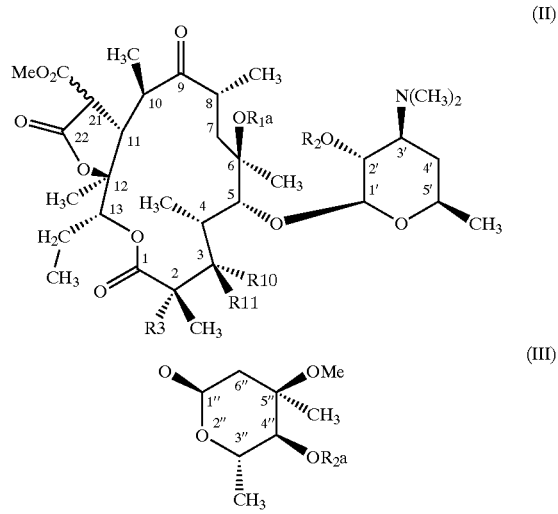

The decarboxylation may be carried out in the presence of a lithium salt such as lithium chloride, preferably in an organic solvent such as dimethylsulphoxide.

Compounds of formula (I), wherein R is cyano, may be prepared by cyclisation of chlorine derivatives (IV) wherein $R_{1a}$, $R_{10}$ and $R_{11}$ have the meaning as defined for compounds of formula (II)

(IV)

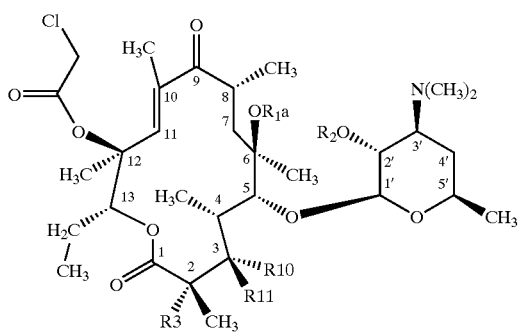

followed, if required, subjecting the resulting compound to one or more of the following operations: a) conversion of the group $R_{1a}$ into the group $R_1$; b) hydrolysis of the cladinose derivative (III); c) conversion of the 3-hydroxy group into the 3-oxo and d) removal of the protecting group $R_2$.

The cyclisation of a compound of formula (IV) is carried out in the presence of potassium cyanide and conveniently in the presence of a solvent such as a N—N dimethylformamide. Alternatively compounds of formula (I) wherein R is hydrogen, may be prepared by elimination of cyano group by treatment of compounds of formula(IVa) with aluminum oxide (IVa)

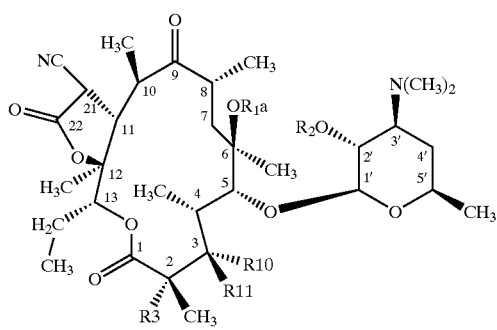

wherein $R_{1a}$, $R_{10}$ and $R_{11}$ have the meaning as defined for compounds of formula (II), followed, if required, subjecting the resulting compound to one or more of the following operations: a) conversion of the group $R_{1a}$ into the group $R_1$; b) hydrolysis of the cladinose derivative (III); c) conversion of the 3-hydroxy group into the 3-oxo and d) removal of the protecting group $R_2$.

Compounds of formula (I), wherein R is $NR_4R_5$, $R_4$ is $C_{1-4}$alkyl and $R_5$ is hydrogen or $C_{1-4}$alkyl, may be prepared by treating amino compounds of formula (V) in which $R_{1a}$, $R_{10}$ and $R_{11}$ have the meaning defined in formula (II)

(V)

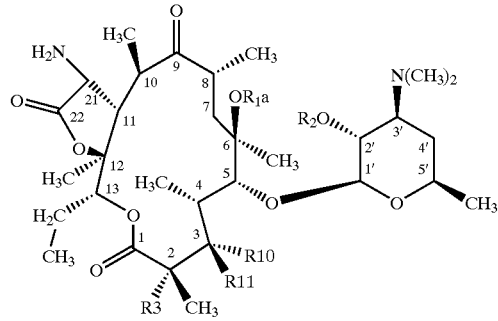

with a suitable alkylating agent of formula L-$R_4$ (VI) wherein $R_4$ is $C_{1-4}$ alkyl and L is a suitable leaving group such as a halogen (e.g. chlorine, bromine or iodine) or a sulfonyl (e.g. tosyl, methansulfonyl), in the presence of a base, followed, if required, subjecting the resulting compound to one or more of the following operations: a) conversion of the group $R_{1a}$ into the group $R_1$; b) hydrolysis of the cladinose derivative (II); c) conversion of the 3-hydroxy group into the 3-oxo and d) removal of the protecting group $R_2$.

Compounds of formula (I), wherein R is $NR_4R_5$, $R_4$ is $C(O)R_5$, may be prepared by treating amino compounds of formula (V) in which $R_{10}$ and $R_{11}$ have the meaning defined in formula (II), by acylation reaction with an activated derivative of the acid $HO(O)CR_5$ (VI a), followed if required, subjecting the resulting compound to one or more of the following operations: a) conversion of the group $R_{1a}$ into the group $R_1$; b) hydrolysis of the cladinose derivative (II); c) conversion of the 3-hydroxy group into the 3-oxo and d) removal of the protecting group $R_2$.

Suitable activated derivatives of the carboxyl group or the sulphonic acid include the corresponding acyl halide, mixed anhydride or activated ester such as a thioester or a pentafluoroester.

The reaction is preferably carried out in the presence of a base such as a tertiary amine e.g. triethylamine or pyridine in a solvent such as a halohydrocarbon e.g. dichloromethane at a temperature within the range 0° to 50° C.

Compounds of formula (I), wherein R is $NH_2$ may be prepared by intramolecular Michael reaction of compounds of formula (VII) wherein $R_{12}$ is a suitable nitrogen protecting group, $R_{1a}$, $R_{10}$ and $R_{11}$ have the meaning defined in formula (II), in the presence of an organic base such as 1,8-diazabicyclo[5.4.0]undec-7-ene, followed, if required, subjecting the resulting compound to one or more of the following operations: a) conversion of the group $R_{1a}$ into the group $R_1$; b) hydrolysis of the cladinose derivative (II); c) conversion of the 3-hydroxy group into the 3-oxo and d) removal of the protecting groups $R_2$ and $R_{12}$.

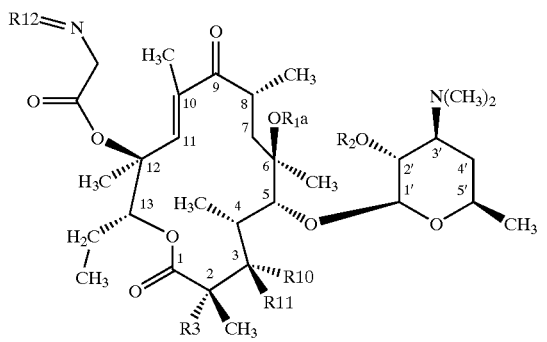

(VII)

The reaction conveniently takes place in an aprotic polar solvent such as acetonitrile, dimethylformamide or an aqueous mixture thereof, followed by removal of the nitrogen protecting group $R_{12}$.

Suitable nitrogen protecting group $R_{12}$ for use in this reaction include diarylmethylidene such as diphenylmethylidene.

When $R_{1a}$ is a group convertible into the group $R_1$ this is suitably $C_{1-10}$ alkyl, $C_{3-10}$ alkenyl or $C_{3-10}$ alkynyl.

The cladinose derivative of formula (III) may be removed by treatment with an organic or inorganic acid. An example of a suitable inorganic acid is hydrochloride. The reaction is carried out in the presence of water or an organic solvent such tetrahydrofuran, dichloromethane or mixture thereof.

The conversion of the 3-hydroxy group into the 3-oxo may be performed by oxidation reaction using a modified Moffatt-Pfitzner procedure.

Suitable oxidizing agents include N,N-Dimethylaminopropyl-3-ethyl carbodiimide-dimethylsulfoxide. The reaction is suitably carried out in the presence of pyridiniumtrifluoro acetate in a chlorinated solvent such as methylene chloride at −10° C. to 25° C.

In a further embodiment, the oxidation may be carried out using Dess Martin periodinane reagent.

Compounds of formula (I) wherein X is a $C_{3-10}$ alkenylene chain and $R_6$ is selected from optionally substituted phenyl, optionally substituted 5 or 6 membered heteroaryl, optionally substituted 9 or 10 membered fused bicyclic aromatic heterocyclic or optionally substituted 9 to 10 membered aromatic fused bicyclic carbocyclic may be prepared by Heck reaction of compounds of formula (VIII),

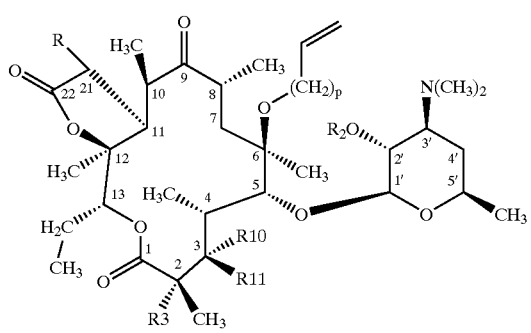

(VIII)

wherein $R_{10}$ and $R_{11}$ have the meaning defined in formula (II), p is an integer from 1 to 8 with a $ZR_6$ (IX) compound wherein Z is a chloride, bromide or triflate.

In one embodiment of this process the reaction may be carried out using a catalytic amount of a Palladium (0) complex such as tetrakis(triaryl phosphine)palladium (e.g. tetrakis(tri-o-tolylphosphine)palladium or tetrakis(triphenyl phosphine)palladium).

The reaction is conveniently carried out in an aprotic solvent such as acetonitrile, dimethylformamide or toluene at a temperature with the range of 60° C. to 150° C.

Compounds of formula (I), wherein X is a $C_{3-10}$ alkenylene chain and $R_6$ is selected from optionally substituted phenyl, optionally substituted 5 or 6 membered heteroaryl, optionally substituted 9 or 10 membered fused bicyclic aromatic heterocyclic or optionally substituted 9 to 10 membered aromatic fused bicyclic carbocyclic, may be prepared by Suzuki reaction of the compounds (X),

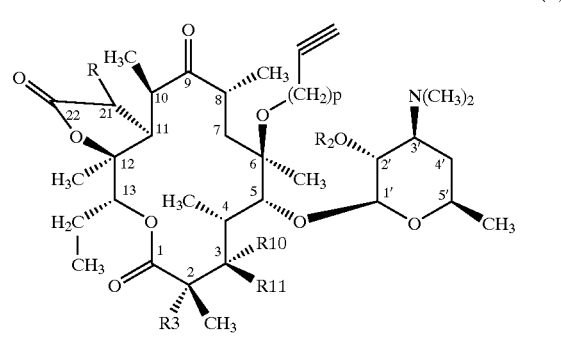

(X)

wherein $R_{10}$ and $R_{11}$ have the meaning defined in formula (II) and p is an integer from 1 to 8, with a boronic acid derivative $R_6B(OH)_2$(Xa), wherein R6 has the meaning defined in formula (IX)

In one embodiment of this process the reaction may be carried out using a catalytic amount of a Palladium (0) complex such as tetrakis(triaryl phosphine)palladium (e.g. tetrakis(tri-o-tolylphosphine)palladium or tetrakis(triphenyl phosphine)palladium).

The reaction is conveniently carried out in an aprotic solvent such as acetonitrile, dimethylformamide or toluene at a temperature with the range of 60° C. to 150° C.

Compounds of formula (I), X is $C_{3-10}$ alkylene optionally substituted as defined in formula (I), may be prepared by reduction of the compound of formula (I) wherein X is $C_{3-10}$ alkenylene.

The reduction may be carried out using hydrogen in the presence of a metal catalyst e.g. palladium on a suitable support e.g. carbon or alumina.

Compounds of formula (I) or compounds of formulas (II), (IV), (IVa) or (V), wherein $R_{1a}$ is $XR_6$, wherein X is $(CH2)_rC(O)(CH2)q$, r is an integer from 1 to 4 and q is an integer from 6 to 9, may be prepared by ozonolysis of a compound of formula (XI), wherein followed by treatment the corresponding aldehyde (XII), with an organo metalic derivative of formula (XIII) $M(CH_2)qR_6$ (XIII), in which M is a metal, and by oxidation of the alcohol (XIII) to the keto group (XIV) according to the following reaction sequence.

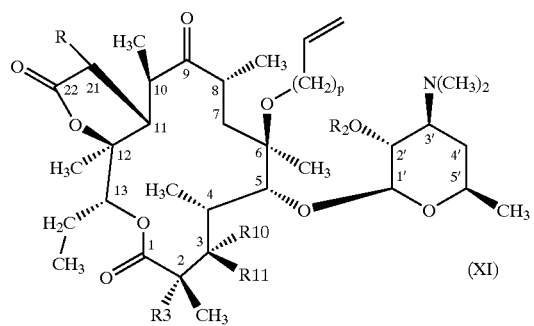

(XI)

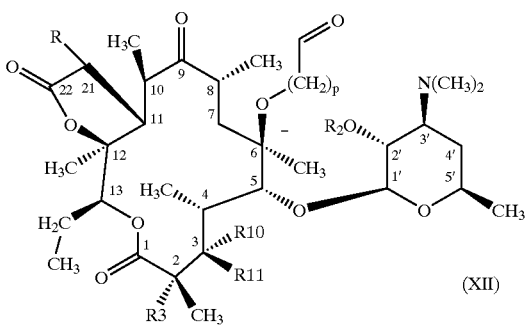

(XII)

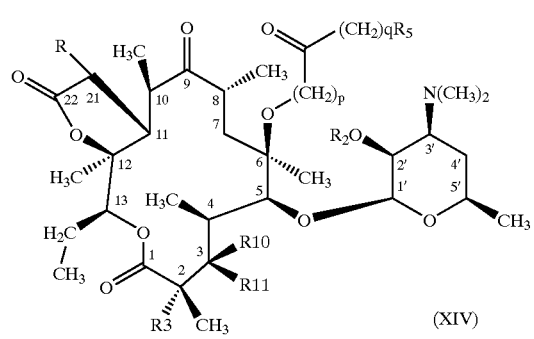

(XIV)

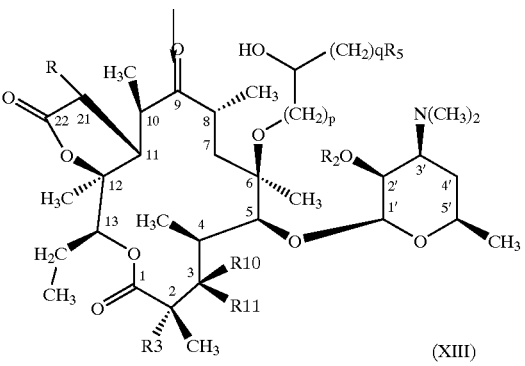

(XIII)

Examples of suitable metal which may be used in this reaction include lithium, zinc or magnesium.

The reaction with compound (XII) is suitably carried out in an aprotic solvent such as toluene, tetrahydrofuran at a temperature ranging from −70° to −20° C.

The oxidation reaction may be carried out using conventional oxidising agents known in the art for converting a secondary alcohol into a ketone. Thus for example the oxidation may be carried out using pyridinium chlorochromate or oxalyl chloride and dimethylsulphoxide. The reaction is preferably carried out in a solvent such as methylene chloride.

Compounds of formula (I) or compounds of formulas (II), (IV), (IVa) or (V), wherein $R_{1a}$ is $XR_6$, wherein X is $(CH2)_rC(O)N(R_5)(CH2)_q$, in which r is an integer from 1 to 4 to form and q is an integer from 6 to 9, may be prepared by oxidation of aldehyde (XII) to the corresponding carboxylic acid (XV), followed by reaction with the amine (XVI) in the presence of an activating agent.

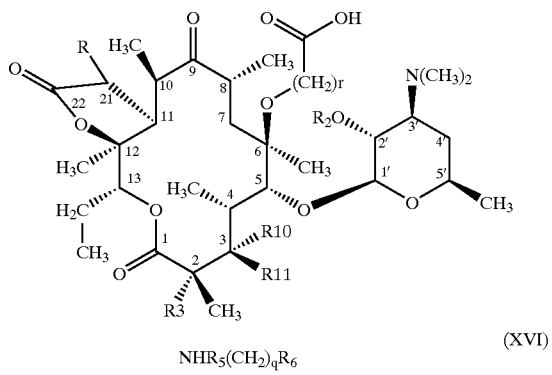

(XV)

NHR$_5$(CH2)$_q$R$_6$ (XVI)

A suitable activating agent of the carboxyl group is for example acyl halide.

Compounds of formula (I) or compounds of formulas (II), (IV), (IVa) or (V), wherein $R_{1a}$ is $XR_6$, wherein X is $(CH2)_rN(R_5)(CH2)_q$, in which r is an integer from 1 to 4, may be prepared by reaction of aldehyde (XII), wherein q is 2 or 3, with amine compounds NHR$_5$(CH2)$_q$R$_6$(XVI).

The reaction is suitably carried out in an aprotic solvent such as dichloromethane and in the presence of a suitable reducing agent such as sodium cyanoborohydride or sodium triacetoxyborohydride.

Compounds of formula (I) or compounds of formulas (II), (IV), (IVa), (V) or (VI) wherein $R_{1a}$ is $XR_6$, wherein X is $(CH2)_rN(R_5)C(O)(CH2)_q$, may be obtained from compounds of formula (I) wherein X is $(CH_2)_rNHR_5$ wherein r is an integer from 2 to 4 and q is an integer from 6 to 9, with the acid (XVII), HOC=O(CH$_2$)$_q$R$_6$ (XVII) and in the resence of an activating agent such as acyl halide.

The reaction is preferably carried out in a suitable aprotic solvent such as a halohydrocarbon (e.g. dichloromethane) or N,N-dimethylformamide optionally in the presence of a tertiary base such as pyridine, dimethylaminopyridine or triethylamine and at a temperature within the range of 0° to 120° C.

A suitable activating agent of the carboxyl group is for example acyl halide.

The hydroxyl protecting groups may be removed by well known standard procedures such as those described in T. W. Greene and P. G. M Wuts in Protective Groups in Organic Synthesis 2$^{nd}$ ed., John Wiley & Son,Inc. 1991. For example when $R_{2a}$ is a trialkyllsilyl group, this may be removed by treatment with tetrabutylammonium fluoride and acetic acid or by reaction with fluoride ions source such as triethyl amine tris (hydrogen fluoride) or this process is conveniently carried out in a solvent such as tetrahydrofuran or acetonitrile. Similarly, when $R_{2a}$ is alkanoyl (i.e. acetyl or benzoyl) these may be removed by treatment with an alcohol (e.g. methanol or ethanol).

Compounds of formula (II) may be prepared by cyclisation of a malonic ester of formula (XVIII), wherein $R_{1a}$ has the meaning defined in formula (II)

(XVIII)

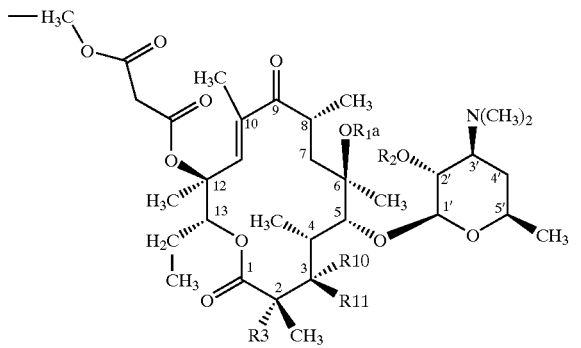

in the presence of a strong base such as 1,8 diazabicyclo [5.4.0]undec-7-ene.

This reaction is conveniently carried out in an organic solvent such acetonitrile, N,N dimethylformamide and the like.

Compounds of formula (XVIII) may be prepared by a reaction of a compounds of formula (XIX), wherein $R_{1a}$ has the meaning defined in formula (II), with a chloride of formula (XX) ClCOCH2COOMe(XX), in the presence of a tertiary base such as pyridine, dimethylaminopyridine or triethylamine and at a temperature within the range of 0° to 30°.

(XIX)

Compounds of formula (IV) may be prepared by a reaction of a compounds of formula (XIX) with a suitable activated derivative of the acid HOCOCH$_2$Cl(XXI).

Thus for example the esterification may be carried out by reaction with anhydride (ClCH$_2$CO)$_2$O (XXII) in a suitable aprotic solvent such as a halohydrocarbon (e.g. dichloromethane) or N,N-dimethylformamide and in the presence of a tertiary base such as pyridine, dimethylaminopyridine or triethylamine and at a temperature within the range of 0° C. to 120° C.

Compounds of formula (VII) may be prepared by treating a compound of formula (IV) with sodium azide, subjecting the resulting azido compound to the following operations: a) reduction by conventional means for reducing azido group to amino group and b) conversion of the group NH$_2$ into the nitrogen protecting group N=$R_{12}$ wherein $R_{12}$ has the meaning defined above and if required by removal of the hydroxy protecting group $R_2$.

Compounds of formula (XIX), may be prepared by reacting 11,12-carbonate, erythromycin A derivatives (XXIII), wherein $R_{2a}$ is a suitable hydroxy protecting group, $R_{10}$ and $R_{11}$ have the meaning defined in formula (II) wherein $R_{1a}$ has the meaning defined in formula (II), with a strong base such as 1,8 diazabicyclo [5.4.0]undec-7-ene.

(XXIII)

The elimination reaction may be carried out in an organic solvent such toluene, ethyl acetate, N,N dimethylformamide or a mixture thereof, conveniently with heating.

Compounds of formula (XXIII), may be prepared from erythromycin A derivatives of formula (XXIV), wherein $R_{1a}$ has the meaning defined in formula (II), (XXIV)

by conversion of the 2'-hydroxy group into the corresponding hydroxy protected group and by conversion of the 11,12 hydroxy into a carbonate group using triphosgene in a suitable solvent such as dicholorometane, in the presence of pyridine.

Compounds of formula (XXIV), wherein $R_{1a}$ is X or $XR_6$ in which X is an optionally substituted $C_{1-10}$ alkylene, an optionally substituted $C_{3-10}$ alkenylene or an optionally substituted $C_{3-10}$ alkynylene, may be prepared by alkylation of an oxime of formula (XXV)

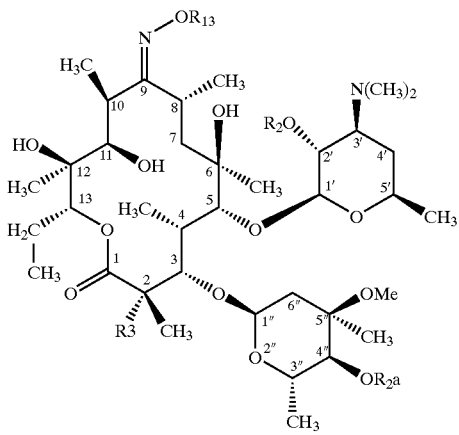

(XXV)

wherein, $R_{13}$ is an oxime protecting group and $R_2$ and $R_{2a}$ is a hydroxyl protecting group, with a compound of formula (XXVI) L-$R_{1a}$ (XXVI) in which L is a suitable leaving group such as a halogen (e.g. chlorine, bromine or iodine) or a sulfonyl (e.g. tosyl, methanesulfonyl), in the presence of a base, followed by hydrolysis of cladinose derivative and conversion of the 3-hydroxy group into the 3-oxo.

The reaction with compound (XXV) is preferably carried out in a solvent such as a halohydrocarbon (e.g. dichloromethane), an ether (e.g. tetrahydrofuran, dimethoxyethane), acetonitrile and the like.

Examples of the bases which may be used include potassium hydroxide, cesium hydroxide, tetraalkylammonium hydroxyde, sodium hydride, potassium hydride and the like, followed by subsequent removal of oxime protecting group.

A suitable oxime protecting group is $R_{13}$, for example, 1-isopropoxycyclohex-1-yl.

Oxime compounds (XXV) may be prepared by reaction of a compound of formula (XXVI) wherein $R_2$ and $R_{2a}$ is hydrogen using analogous methods to those described in U.S. Pat. No. 6,110,965.

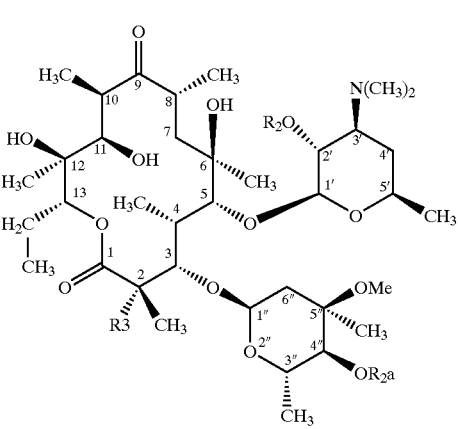

(XXVI)

Compounds of formula (I) wherein $R_3$ is halogen may be prepared from compounds of formula (I) in which $R_3$ is hydrogen and $R_2$ is hydroxy protecting group by reaction with a halogenating agent in the presence of an organic or inorganic base.

Suitable halogenating agents include N-fluoro benzensulfonimide, SELECTFLUOR™ for fluorination, pyridinium tribromide or cyanogen bromide for bromination or hexachloroethane for chlorination.

A convenient base for the reaction is selected from sodium hydride, potassium hydride, sodium carbonate, potassium hexamethyldisilazide, lithium diisopropylamide or pyridine. The reaction is carried out in a solvent such as N,N dimethylformamide, tetrahydrofuran or N-methylpyrrolidone or a mixture thereof, conveniently at a temperature within the range −78° to 60° C.

Alternatively the halo group in position 2 of the macrolide ring may be introduced in an earlier step of the synthesis of compounds of formula (I). Thus, for example, it may be introduced by treating a compound of formulas (II), (IV), (IVa), (V), (VII), (VIII), (X), (XI), (XII), (XIII), (XIV), (XV), (XVIII), (XIX), (XXIII) or (XXIV) provided that $R_{10}$ together with $R_{11}$ is an oxygen atom, using the method above described for obtaining compounds of formula (I) wherein $R_3$ is a halo group.

Compounds of formulas (VI), (VIa), (IX), (XVI), (XVII), (XX), (XXI) or (XXII) may be prepared using methods known in the art.

The nitrogen protection reaction may be carried out with an appropriate imine such as benzophenone imine in an aprotic solvent, e.g. dichloromethane, preferably at room temperature.

Where it is desired to isolate a compound formula (I) as a salt thereof, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compound of formula (I) using conventional methods.

Suitable hydroxy protecting reagent are those described by T. W. Greene and P. G. M Wuts in Protective Groups in Organic Synthesis $2^{nd}$ ed., John Wiley & Son, Inc 1991, which is incorporating by reference. Examples of suitable hydroxy protecting reagents include acetic anhydride, benzoic anhydride or a trialkylsilyl chloride in a protic solvent. Examples of aprotic solvent are dichloromethane, NN-dimethylformamide, dimethylsulfoxide, tetrahydrofuran and the like.

The hydroxyl protecting groups may be removed by well known standard procedures. For example when $R_{2a}$ is a trialkyllsilyl group, this may be removed by treatment with tetrabutylammonium fluoride and acetic acid or by reaction with fluoride ions source such as triethyl amine tris (hydrogen fluoride) or this process is conveniently carried out in a solvent such as tetrahydrofuran or acetonitrile. When $R_2$ or $R_{2a}$ is alkanoyl (i.e acetyl or benzoyl) these may be removed by treatment with an alcohol (e.g. methanol or ethanol).

The nitrogen protecting group may be removed by well known standard procedures such as those described in T. W. Greene and P. G. M Wuts in Protective Groups in Organic Synthesis $2^{nd}$ ed., John Wiley &Son, Inc. 1991. Thus for example when $R_8$ and $R_9$ indipendently represent alkoxycarbonyl group may be removed by acid hydrolisis.

In any of the formulae (I), (II), (IVa), (VIII), (X), (XI), (XII), (XIII), (XIV) or (XV) shown above when there is an asymmetric carbon atom and no specific configuration is shown then the formula includes all possible configurations.

Specific stereoisomers of the compounds of formula (I) as defined in formula 1a and 1b essentially free of the other stereoisomers may be prepared using general processes described above starting with the appropriate stereisomer of formula (IV).

The process described above for preparing the compounds of formula (I) will in general give a mixture of diastereoisomers 1a and 1b.

The individual stereoisomers of the compounds of formula (I) may be separated each other by conventional techniques such as fractional crystallisation or more particularly by column chromatography, using for example a silica column.

In a preferred embodiment of the invention the individual stereoisomer of formula (1a) wherein R is $NH_2$ may be prepared by epimerisation reaction of a compound of formula(1b) or mixture of (1a) and (1b) wherein R is $NH_2$. The reaction is carried out in the presence of benzaldehyde and DBU, followed by hydrolysis of the imine derivative with inorganic acid such as hydrochloride. The reaction is suitable carried out in aprotic solvent such as for example toluene, N-N dimethylformamide.

The assignment of the R or S configuration at the 21-position have been made according to the rules of Cahn, Ingold and Prelog, Experientia 1956, 12, 81.

When examples are obtained as a diastereoisomeric mixture of 21R and 21S, unless otherwise stated, the $^1$H-NMR spectra refers to the $^1$H-NMR spectra of the predominant diastereoisomer (i.e. 21 S).

The invention is further illustrated by the following Intermediates and Examples which are not intended as a limitation of the invention.

In the Intermediates and Examples unless otherwise stated:

Proton Magnetic Resonance ($^1$H-NMR) spectra were recorded at 500 Mz, chemical shifts are reported in ppm downfield (δ) from $Me_4Si$, used as internal standard, and are assigned as singlets (s), doublets (d), doublets of doublets (dd), triplets (t), quartets (q) or multiplets (m). Mass spectra were acquired with a Hewlett Packard 1100 MSD Mass Spectrometer in positive electrospray ionisation.

Column chromathography was carried out over silica gel 60 (230–400 mesh ASTM-Merck AG Darmstaadt, Germany). The TLC (Thyn Layer Chromatography) monitoring was performed using Merck 60 $F_{254}$ as TLC plate.

Abbreviations which have been used in the description of the synthetic methods that follow are: DBU 1,8-diazabicyclo [5.4.0]undec-7-ene, DCM for dichloromethane, DIPEA for N,N-diisopropylethylamine, DMAP for 4-dimethylaminopyridine, DMF for N,N-dimethylformamide, DMSO for methyl sulfoxide, EDC for 1-(3-dimethylaminopropyl)-3-ethylcarbodiimide hydrochloride, $Et_2O$ for diethyl ether, EtOAc for ethyl acetate, HATU for O-(7-azabenzotriazol-1-yl)-N,N,N',N'-tetramethyluronium hexafluorophosphate, MeOH for methanol, TEA for triethylamine and THF for tetrahydrofuran, wt for weight.

Intermediate 1

2',4"-O-Diacetyl-6-O-allyl-erythromycin A

To a solution of 6-OAllyl erythromycin A (1 g) in anhydrous DCM (5 mL) cooled to 0° C. TEA (0.5 mL), DMAP (0.008 g) and acetic anhydride (0.31 mL) were added under nitrogen atmosphere. The resulting mixture was stirred at 0° C. for 1 h and overnight at room temperature. Then the mixture was diluted with a saturated $NH_4Cl$ aqueous solution (30 mL) and extracted with DCM (2×50 mL). The aqueous phase was neutralised with a saturated $NaHCO_3$ aqueous solution and extracted again with DCM (2×50 mL). The combined organic layers were dried over $Na_2SO_4$ and evaporated under reduced pressure to give the title compound (1 g) as white foam.

m\z ([MH]$^+$)=858.

Intermediate 2

11,12-Carbonate-2',4"-O-diacetyl-11,12-dideoxy-6-O-allyl-erythromycin A

To a solution of intermediate 1 (4.13 g) in anhydrous DCM (85 mL) cooled to 0° C., pyridine (0.8 mL) and then phosgene (20% sol in toluene, 2.55 mL) were added under nitrogen atmosphere. The resulting mixture was stirred at 0° C. for 30 min and then at room temperature for 1 h. The reaction mixture was then diluted with water (150 mL) and extracted with DCM (2×200 mL). The organic layer was washed with water (3×100 mL), dried over $Na_2SO_4$ and evaporated under reduced pressure to give the title compound (4.02 g).

m\z ([MH]$^+$)=884.

Intermediate 3

11-Deoxy-2',4"-O-diacetyl-10,11-didehydro-6-O-allyl-erythromycin A

To a solution of intermediate 2 (4.02 g) in toluene (45 mL) and EtOAc (23 mL), DBU (0.71 mL) was added at room temperature. The resulting mixture was stirred at 85° C. for 6 h. The mixture was then diluted with brine (100 mL), extracted with EtOAc (2×200 mL) and dried over $Na_2SO_4$. Solvent evaporation under reduced pressure and purification by flash chromatography (eluting with: DCM/MeOH/$NH_4OH$ 95/4/0.01) gave the title compound (1.70 g).

m\z ([MH]$^+$)=840.

Intermediate 4

12-Chloroethanoyl-11-deoxy-2',4"-O-diacetyl-10,11-didehydro6-O-allyl-erythr mycin A To a solution of intermediate 3 (1.7 g) in anhydrous DCM (50 mL) cooled to 0° C., pyridine (0.66 mL), DMAP (0.012 g) and chloroacetic anhydride (0.695 g) were added under nitrogen atmosphere. The resulting mixture was stirred for 30 min at 0° C. and then at room temperature for 2.5 h. The mixture was diluted with water (50 mL), neutralised with a saturated $NaHCO_3$ aqueous solution and extracted with DCM (2×100 mL). The organic phase was washed with water (3×50 mL), dried over $Na_2SO_4$ and evaporated under reduced pressure to give the title compound (1.8 g).

m\z ([MH]$^+$)=916.

Intermediate 5

2'-O-Acetyl-12-chloroethanoyl-3-decladinosyl-11-deoxy-10,11-didehydro-6-O-allyl-erythromycin A To a solution of intermediate 4 (1.8 g) in THF (35 mL), a 6N HCl aqueous solution (10 mL) was added at 0° C. The resulting mixture was stirred overnight at room temperature and then was diluted with water (50 mL). The pH of the solution was brought to 8–9 by addition of solid $NaHCO_3$ and 1% NaOH aqueous solution and then the aqueous phase was extracted with DCM (2×100 mL). Solvent evaporation under reduced pressure and treatment of the crude material with $Et_2O$ gave the title compound (1.4 g).

m\z([MH]$^+$)=716.

Intermediate 6

(11S,21R)-2'-O-Acetyl-3-decladinosyl-11,12-dideoxy-6-O-allyl-12,11-[oxycarbonyl-(cyano)-methylene]-erythromycin A To a solution of intermediate 5 (1.3 g) in anhydrous DMF (40 mL) potassium cyanide (0.500 g) was added under nitrogen atmosphere. The reaction mixture was stirred at room temperature for 1 h, quenched with a 5% NaHCO$_3$ aqueous solution (50 mL) and extracted with DCM (2×50 mL). Purification of the crude material by flash chromatography (eluting with: DCM/MeOH/NH$_4$OH 95/4/0.01) gave the title compound (0.42 g).

m\z ([MH]$^+$)=707.

Intermediate 7

2'-O-Acetyl-11,12-carbonate-3-decladinosyl-11,12-dideoxy-6-O-methyl-3-oxo-erythromycin A To a solution of 2'-O-acetyl-3-decladinosyl-6-O-methyl-3-oxo-erythromycin A (0.500 g) in anhydrous DCM (20 mL) pyridine (1.5 mL) and phosgene (20% sol. in toluene, 1 mL) were sequentially added under nitrogen atmosphere. The reaction mixture was stirred overnight at room temperature, then quenched with a saturated NaHCO$_3$ aqueous solution (50 mL) and washed with water (50 mL). The organic phase was dried over Na$_2$SO$_4$ and concentrated under reduced pressure. Purification of the crude material by flash chromatography (eluting with: DCM/MeOH 9/1) gave the title compound (0.360 g).

TLC: DCM/MeOH 9/1 (Rf=0.6).

Intermediate 8

2'-O-Acetyl-3-decladinosyl-11-deoxy-10,11-didehydro-6-O-methyl-3-oxo-erythromycin A To a solution of intermediate 7 (0.210 g) in 2/1 mixture of EtOAc/toluene (6 mL) DBU (0.05 mL) was added and the mixture was heated to 85° C. for 6 h. The solution was allowed to reach room temperature and the solvent evaporated under reduced pressure. Purification of the crude material by flash chromatography (eluting with: DCM/MeOH 9/1) gave the title compound (0.150 g).

TLC: DCM/MeOH 9/1 (Rf=0.7).

Intermediate 9

2'-O-Acetyl-12-chloroethanoyl-3-decladinosyl-11-deoxy-10,11-didehydro-6-O-methyl-3-oxo-erythromycin A To a solution of intermediate 8 (0.150 g) in anhydrous DCM (3 mL) cooled at 0° C., pyridine (0.05 mL), chloroacetic anhydride (0.065 g) and DMAP (5 mg) were sequentially added under nitrogen atmosphere. The reaction mixture was stirred for 4 h then quenched with water (10 mL) and extracted with DCM (2×10 mL). The organic phase was dried over Na$_2$SO$_4$, concentrated under reduced pressure and purified by flash chromatography (eluting with: DCM/MeOH 8/2) to give the title compound (0.060 g).

TLC: DCM/MeOH 9/1 (Rf=0.8).

Intermediate 10

2',4"-O-Diacetyl-6-O-methyl-erythromycin A

To a solution of 6-O-methyl-erythromycin A (50 g) in anhydrous DCM (240 mL) cooled to 0° C., TEA (26.1 mL), DMAP (0.392 g) and acetic anhydride (15.2 mL) were added under nitrogen atmosphere. The resulting mixture was stirred at 0° C. for 45 min and overnight at room temperature. The mixture was then diluted with a NH$_4$Cl saturated aqueous solution (200 mL) and extracted with DCM (2×200 mL). The aqueous phase was neutralised with a saturated NaHCO$_3$ aqueous solution and extracted again with DCM (2×200 mL). The combined organic layers were dried over Na$_2$SO$_4$ and evaporated under reduced pressure to give the title compound (50.7 g).

m\z([MH]$^+$)=832.

Intermediate 11

11,12-Carbonate-2',4"-O-diacetyl-11,12-dideoxy-6-O-methyl-erythromycin A

To a solution of intermediate 10 (25.4 g) in anhydrous DCM (200 mL) cooled to 0° C., pyridine (15 mL) and a solution of triphosgene (9 g) in anhydrous DCM (50 mL) were added under nitrogen atmosphere. The resulting mixture was stirred at 0° C. for 30 min and then at room temperature overnight. The mixture was then diluted with water (200 mL) and extracted with DCM (2×300 mL). The organic layer was washed with water 3×100 mL), dried over Na$_2$SO$_4$ and evaporated under reduced pressure to give the title compound (25.5 g).

m\z ([MH]$^+$)=858.

Intermediate 12

11-Deoxy-2',4"-O-diacetyl-10,11-didehydro-6-O-methyl-erythromycin A

To a solution of intermediate 11 (50.5 g) in 2/1 mixture of toluene/EtOAc (675 mL), DBU (9.24 mL) was added at room temperature. The resulting mixture was heated to 85° C. for 8 h and at room temperature for 5 h. The mixture was then diluted with brine (200 mL) and extracted with EtOAc (3×200 mL). The organic phase was dried over Na$_2$SO$_4$ and concentrated under reduced pressure. Crystallisation from acetone/water gave the title compound (46 g).

m\z ([MH]$^+$)=814.

Intermediate 13

11-Deoxy-2',4"-O-diacetyl-10,11-didehydro-12-methoxycarbonylethanoyl-6-O-methyl-erythromycin A To a solution of intermediate 12 (0.500 g) in anhydrous toluene (100 mL) and pyridine (0.250 mL) cooled to 0° C. methylmalonyl chloride (0.158 mL) was added. The temperature was allowed to reach room temperature and after stirring 1 hr, water (50 mL) was added. The organic layer was washed with brine (50 mL), dried over Na$_2$SO$_4$ and concentrated under reduced pressure. Purification of the crude material by quick filtration through a filter of silica gel gave the title compound (0.560 g).

m\z ([MH]$^+$)=914.

Intermediate 14

2'-O-Acetyl-3-decladinosyl-11-deoxy-10,11-didehydro-12-metboxycarbonylethanoyl-6-O-methyl-erythromycin A and

Intermediate 15

2'-O-Acetyl-3-decladinosyl-11-deoxy-10,11-didehydro-12-carboxyethanoyl-6-O-methyl-erythromycin A Intermediate 13 (0.500 g) was stirred in a 2N HCl aqueous solution (50 mL) and THF (1 mL) at room temperature for 6 h. Then the mixture was cooled to 0° C. and a saturated K₂CO₃ aqueous solution was added until pH=9 was obtained. The aqueous phase was extracted with DCM (2×50 mL), the organic phase was washed with brine (50 mL), dried over Na₂SO₄ and concentrated under reduced pressure. The crude material was purified by flash chromatography (eluting with: DCM/MeOH=95/5) to give the title compound 14 (0.180 g) and the title compound 15 (0.180 g).

m\z ([MH]$^+$) (14)=714.

m\z ([MH]$^+$) (15)=680.

Intermediate 16

(10R,S,11S,21R,S)-2'-O-Acetyl-3-decladinosyl-11, 12-dideoxy-6-O-methyl-12,11-[oxycarbonyl-(methoxycarbonyl)-methylene]-erythromycin A A solution of intermediate 14 (0.150 g) in water (1.5 mL), acetonitrile (13.5 mL) and DBU (0.050 mL) was stirred at 40° C. for 6 h. After evaporating the solvent under reduced pressure, the residue was dissolved in DCM (20 mL) and washed with water (50 mL). The organic phase was dried over Na₂SO₄ and concentrated under reduced pressure. The crude material was purified by flash chromatography (eluting with: DCM/MeOH 95/5) to give the title compound (0.070) g.

m\z ([MH]$^+$)=714.

Intermediate 17

(10R,S,11R)2'-O-Acetyl-3-decladinosyl-11,12-dideoxy-6-O-methyl-12,11-[oxycarbonylmethylene]-erythromycin A A stirred mixture of intermediate 16 (0.050 g) and lithium chloride (6 mg) in DMF (1 mL) was refluxed for 4 h. The reaction mixture was allowed to reach room temperature, then poured into an iced solution of a 3% NaHCO₃ aqueous solution and the aqueous phase extracted with DCM (2×15 mL). The organic phase was washed with water (2×10 mL), dried over Na₂SO₄ and concentrated under reduced pressure. The crude material was purified by flash chromatography (DCM/MeOH: 95/5) to give the title compound (0.010 g)

m\z ([MH]$^+$)=656.

Intermediate 18

2'-O-Acetyl-12-azidoethanoyl-3-decladinosyl-11-deoxy-10,11-didehydro-6-O-allyl-erythromycin A To a solution of intermediate 5 (1.42 g) in anhydrous DMF (110 mL), sodium azide (0.211 g) was added under nitrogen atmosphere. The mixture was heated to 80° C. for 10 min then quenched with water (100 mL) and extracted with EtOAc (3×200 mL). The organic layer was dried over Na₂SO₄ and concentrated under vacuum to give the title compound (1.36 g).

m\z ([MH]$^+$)=723.

Intermediate 19

2'-O-Acetyl-12-aminoethanoyl-3-decladinosyl-11-deoxy-10,11-didehydro-6-O-allyl-erythromycin A To a solution of intermediate 18 (1.36 g) in THF (25 mL), triphenylphosphine (0.985 g) and water (0.034 mL) were added. The mixture was stirred at room temperature overnight. After evaporating the solvent, the crude material was dissolved in DCM (100 mL) and washed with water (2×100). The organic layer was dried over Na₂SO₄ and concentrated under vacuum to give the title compound (1.3 g).

m\z ([MH]$^+$)=697.

Intermediate 20

2'-O-Acetyl-12-(benzhydrylidene)-aminoethanoyl-3-decladinosyl-11-deoxy-10,11-didehydro-6-O-allyl-erythromycin A A solution of intermediate 19 (1.3 g) and benzophenone imine (0.9 mL) in anhydrous DCM (15 mL) was stirred at room temperature. After 30 h the reaction was quenched with water (50 mL) and extracted with DCM (3×100 mL). The organic layer was dried over Na₂SO₄ and concentrated under vacuum to give the title compound (1.6 g).

m\z ([MH]$^+$)=861.

Intermediate 21

(11S,21R,S)-2'-O-Acetyl-3-decladinosyl-11,12-dideoxy-6-O-allyl-12,11-[oxycarbonyl-(benzhydrylideneamino)-methylene]-erythromycin A A solution of intermediate 20 (1.6 g) and DBU (0.3 mL) in acetonitrile (90 mL) and water (9 mL) was stirred at room temperature. After evaporating the solvent, the crude material was dissolved in DCM (100 mL). The organic phase was washed with water (2×100 mL), dried over Na₂SO₄ and concentrated under vacuum. The crude material was purified by flash chromatography (eluting with: DCM/MeOH/NH₃ 9.5/0.4/0.03) to give the title compound (0.528 g).

m\z ([MH]$^+$)=861.

Intermediate 22

(11S,21R,S)-2'-O-Acetyl-3-decladinosyl-11,12-dideoxy-6-O-allyl-3-oxo-12,11-[oxycarbonyl-(benzhydrylideneamino)-methylene]-erythromycin A To a solution of intermediate 21 (0.528 g) and EDC (0.70 g) in DCM anhydrous (40 mL) cooled to 0° C., DMSO (0.8 mL) was added under nitrogen atmosphere. After 10 min at 0° C., a solution of pyridinium trifluoroacetate (0.72 g) in DCM (2 mL) was slowly added. After 10 min the ice bath was removed and the mixture stirred for 1 h. The reaction mixture was quenched with water (50 mL) and extracted with DCM (3×100 mL). The organic layer was dried over Na₂SO₄ and concentrated under vacuum to give the title compound (0.520 g).

TLC: DCM/MeOH/NH₃ 20/2/0.2 (Rf=0.39).

Intermediate 23

12-Chloroethanoyl-11-deoxy-2',4"-O-diacetyl-10,11-didehydro-6-O-methyl-erythromycin A To a solution of intermediate 12 (20 g) in anhydrous DCM (340 mL) cooled to 0° C., pyridine (6 mL) and chloroacetic anhydride (8.4 g) were added under nitrogen atmosphere and the reaction was allowed to reach room temperature. After 18 h the reaction was quenched with water (300 mL), the organic phase washed with a saturated NH₄Cl aqueous solution (150 mL) and brine (150 mL), the aqueous phase extracted again with DCM (2×300 mL). The combined organic layers were dried over Na₂SO₄ and concentrated under reduced pressure. Crystallisation of the crude material from acetone/water gave the title compound (20.4 g).

m\z ([MH]⁺)=890.

Intermediate 24

2'-O-Acetyl-12-chloroethanoyl-3-decladinosyl-11-deoxy-10,11-didehydro-6-O-methyl-erythromycin A To a solution of intermediate 23 (20.2 g) in THF (200 mL) cooled to 0° C. a 3N HCl aqueous solution (400 mL) was added dropwise. Then the reaction was allowed to reach room temperature and stirred overnight. The solution was neutralised with a saturated NaHCO₃ aqueous solution and extracted with DCM (2×250 mL). The organic phase was dried over Na₂SO₄ and concentrated under reduced pressure. The crude material was purified by quick filtration through a silica pad to give the title compound (15.4 g).

m\z ([MH]⁺)=690.

Intermediate 25

2'-O-Acetyl-12-azidoethanoyl-3-decladinosyl-11-deoxy-10,11-didehydro-6-O-methyl-erythromycin A To a solution of intermediate 24 (4.2 g) in anhydrous DMF (170 mL), sodium azide (0.600 g) was added under nitrogen atmosphere. The mixture was heated to 80° C. for 1 hr then quenched with water (150 mL) and extracted with EtOAc (3×300 mL). The organic layer was dried over Na₂SO₄, filtered and concentrated under vacuum to give the title compound (4.2 g).

m\z ([MH]⁺)=697.

Intermediate 26

2'-O-Acetyl-12-aminoethanoyl-3-decladinosyl-11-deoxy-10,11-didehydro-6-O-methyl-erythromycin A To a solution of intermediate 25 (4.2 g) in THF (75 mL), triphenylphosphine (1.6 g) was added. After stirring at room temperature overnight water (3 mL) was added and the reaction mixture stirred for 6 hr. After evaporating the solvent, the crude material was dissolved in DCM (400 mL) and washed with water (2×200). The organic layer was dried over Na₂SO₄ and concentrated under vacuum to give the title compound (4.0 g).

TLC: DCM/MeOH 10/1 (Rf=0.28).

Intermediate 27

2'-O-Acetyl-12-(benzhydrylidene)-aminoethanoyl-3-decladinosyl-11-deoxy-10,11-didehydro-6-O-methyl-erythromycin A A solution of intermediate 26 (4.0 g) and benzophenone imine (2.6 mL) in anhydrous DCM (40 mL) was stirred at room temperature. After 36 h the reaction was quenched with water (100 mL) and extracted with DCM (3×300mL). The organic layer was dried over Na₂SO₄ and concentrated under vacuum. The crude material was purified by flash chromatography (eluting with: DCM/MeOH 95/5) to give the title compound (3.5 g).

TLC: DCM/MeOH 10/1 (Rf=0.38).

Intermediate 28

(11S,21R,S)-2'-O-Acetyl-3-decladinosyl-11,12-dideoxy-6-O-methyl-12,11-[oxycarbonyl-(benzhydrylideneamino)-methylene]-erythromycin A A solution of intermediate 27 (3.0 g) and DBU (0.540 mL) in acetonitrile (135 mL) and water (15 mL) was stirred at room temperature for 3 h. After evaporating the solvent, the crude material was dissolved in DCM (300 mL) and washed with water (100 mL). The organic layer was dried over Na₂SO₄ and concentrated under vacuum to give the title compound (2.9 g).

TLC: DCM/MeOH 10/1 (Rf=0.38).

Intermediate 29

(11S,21R,S)-2'-O-Acetyl-3-decladinosyl-11,12-dideoxy-6-O-methyl-3-oxo-12,11-[oxycarbonyl-(benzhydrylideneamino)-methylene]-erythromycin A To a solution of intermediate 28 (1.5 g) and EDC (3.10 g) in DCM (100 mL) cooled to 0° C., DMSO (3.45 mL) was added. After 10 min. at 0° C., a solution of pyridinium trifluoroacetate (3.12 g) in DCM (15 mL) was slowly added under nitrogen atmosphere. After 10 min the ice bath was removed. The reaction mixture was stirred for 3 h then quenched with water (150 mL) and extracted with DCM (3×250 mL). The organic layer was dried over Na₂SO₄ and concentrated under vacuum. The crude material was purified by flash chromatography (eluting with: DCM/MeOH 95/5) to give the title compound (1.2 g).

¹H-NMR (CDCl₃) δ: 7.8–7.2 (m, 10H), 6.40 (dd, 1H), 5.15 (s, 1H), 4.73 (m, 1H), 4.42 (d, 1H), 4.16 (d, 1H), 3.90 (q, 1H), 3.55 (m, 1H), 3.17 (m, 1H), 2.95 (m, 1H), 2.94 (d, 1H), 2.67 (m, 1H), 2.53 (s, —OCH₃), 2.43 (m, 1H), 2.33 (s, N(CH₃)₂), 2.05 (s, 3H), 2.00 (m, 1H), 1.74 (m, 1H), 1.65 (m, 1H), 1.53 (s, 3H), 1.38 (d, 3H), 1.23 (s, 3H), 1.29 (d, 3H), 1.25 (m, 1H), 1.25 (d, 3H), 1.14 (d, 3H), 1.07 (d, 3H), 0.83 (t, 3H). TLC: DCM/MeOH 10/1 (Rf=0.30).

Intermediate 30

Trifluoro-methanesulfonic acid quinolin-5-yl ester

To a suspension of quinolin-5-ol (0.300 g) in anhydrous DCM (12 ml) cooled to −30° C. 2,6-dimethyl-pyridine (0.257 g), DMAP (0.050 g) and trifluoromethensulfonic anhidride (0.670 g) were sequentally added. The temperature was allowed to reach room temperature and the reaction mixture was stirred overnight. The mixture was poured into a saturated NaHCO₃ aqueous solution (15 ml), extracted with EtOAc (3×15 ml). The organic phase was dried over Na₂SO₄ and concentrated under reduced pressure. The crude material was purified by flash chromatography (eluting with: cyclohexane/EtOAc from 7/3 to 6/4) to give the title compound (0.197 g).

m\z ([MH]⁺)=278.

Intermediate 31

Trifluoro-methanesulfonic acid quinolin-6-yl ester

To a suspension of quinolin-6-ol (0.500 g) in anhydrous DCM (20 ml) cooled to −30° C. 2,6-dimethyl-pyridine (0.46 ml), DMAP (0.084 g) and trifluoromethensulfonic anhidride (0.67 ml) were sequentally added. The temperature was allowed to reach room temperature and the reaction mixture was stirred overnight. The mixture was diluted with a saturated NaHCO₃ aqueous solution (35 ml), extracted with EtOAc (3×50 ml). The organic phase was washed with brine (50 ml), dried over Na₂SO₄ and concentrated under reduced pressure. The crude material was purified by flash chromatography (eluting with: cyclohexane/EtOAc 8/2) to give the title compound (0.210 g).

TLC: cyclohexane/EtOAc 2/8 (Rf=0.70)

m\z ([MH]⁺)=278.

Intermediate 32

Trifluoro-methanesulfonic acid quinolin-7-yl ester

To a solution of quinolin-7-ol (0.500 g) in anhydrous pyridine (2.5 ml) cooled to 0° C. trifluoromethensulfonic anhydride (0.64 ml) was added and the mixture stirred at 0° C. for 5 min. The temperature was allowed to reach room temperature and the reaction mixture was stirred for 3 h. The mixture was diluted with a 1M aqueous HCl solution (25 ml) and extracted with Et$_2$O (3×50 ml). The organic phase was washed with brine (50 ml), dried over Na$_2$SO$_4$ and concentrated under reduced pressure. The crude material was purified by flash chromatography (eluting with: cyclohexane/EtOAc 3/7) to give the title compound (0.770 g).

m\z ([MH]$^+$)=278.

Intermediate 33

(11S,21R)-2'-O-Acetyl-3-decladinosyl-11,12dideoxy-6-O-allyl-3-oxo-12,11-[oxycarbonyl-(cyano)-methylene]-erythromycin A To a solution of intermediate 6 (0.33 g) in DCM (30 mL) Dess-Martin periodinane (0.300 g) was added portionwise within 3 h. A solution of Na$_2$S$_2$O$_3$ (5% in a saturated NaHCO$_3$ aqueous solution, 20 mL) was added and the mixture was stirred for 1 h. The aqueous phase was extracted with DCM (2×50 mL), the organic phase washed with water (50 mL), dried over Na$_2$SO$_4$ and concentrated under reduced pressure. Purification of the crude material by flash chromatography (eluting with: DCM/MeOH/NH$_3$ 9.6/0.3/0.09) gave the title compound (0.13 g).

$^1$H-NMR (CDCl$_3$) δ: 5.69 (m, 1H), 5.43 (dd, 1H), 5.09 (m, 2H), 4.75 (m, 1H), 4.73 (s, 1H), 4.47 (d, 1H), 4.39 (d, 1H), 3.91 (q, 1H), 3.70 (m, 2H), 3.63 (m, 1H), 3.21 (m, 1H), 3.20 (s, 1H), 3.12 (m, 1H), 2.70 (m, 1H), 2.65 (m, 1H), 2.26 (s, N(CH$_3$)$_2$), 2.04 (s, 3H), 1.94 (m, 1H), 1.70 (m, 1H), 1.65 (m, 1H), 1.60 (s, 3H), 1.55 (m, 1H), 1.36 (d, 3H), 1.33 (s, 3H), 1.26 (d, 6H), 1.13 (d, 3H), 1.06 (d, 3H), 0.93 (t, 3H).

Intermediate 34

(11S,21R)-3-Decladinosyl-11,12-dideoxy-6-O-allyl-3-oxo-12,11-[oxycarbonyl-(cyano)-methylene]-erythromycin A A solution of intermediate 33 (0.005 g) in MeOH (0.5 mL) was stirred at room temperature overnight. Solvent evaporation under reduced pressure gave the title compound (0.003 g).

$^1$H-NMR (CDCl$_3$) δ: 5.71 (m, 1H), 5.44 (dd, 1H), 5.08 (m, 2H), 4.72 (s, 1H), 4.43 (d, 1H), 4.40 (d, 1H), 3.94 (q, 1H), 3.72 (m, 2H), 3.62 (m, 1H), 3.20 (m, 4H), 2.68 (m, 1H), 2.52 (m, 1H), 2.29 (s, N(CH$_3$)$_2$), 1.94 (m, 1H), 1.81 (m, 1H), 1.65 (m, 1H), 1.60 (m, 1H), 1.61 (s, 3H), 1.42 (d, 3H), 1.35 (s, 3H), 1.34 (d, 3H), 1.26 (d, 3H), 1.12 (d, 3H), 1.08 (d, 3H), 0.93 (t, 3H).

Intermediate 35

(11S,21R)-2'-O-Acetyl-3-decladinosyl-11,12-dideoxy-6-O-methyl-3-oxo-12,11-[oxycarbonyl-(cyano)-methylene]-erythromycin A To a solution of intermediate 9 (0.060 g) in anhydrous DMF (16 mL) potassium cyanide (0.051 g) was added under nitrogen atmosphere. The reaction mixture was stirred at room temperature for 2 h, quenched with a saturated NaHCO$_3$ aqueous solution (30 mL) and extracted with DCM (3×30 mL). The organic phase was then washed with brine (30 mL), dried over Na$_2$SO$_4$ and evaporated under reduced pressure. Purification of the crude material by flash chromatography (eluting with: DCM/MeOH 95/5) gave the title compound (0.017 g).

$^1$H-NMR (CDCl$_3$) δ: 5.27(dd, 1H), 4.74 (dd, 1H), 4.62 (d, 1H), 4.42 (d, 1H), 4.26 (d, 1H), 3.84 (q, 1H), 3.56 (m, 1H), 3.16 (m, 1H1), 3.10–3.0 (m, 2H), 2.77 (s, —OCH$_3$), 2.68 (m, 1H), 2.60 (m, 1H), 2.25 (s, N(CH$_3$)$_2$), 2.05 (m, 3H), 1.90 (m, 1H), 1.68 (m, 1H), 1.63 (m, 2H), 1.56 (s, 3H), 1.39 (d, 3H), 1.35 (m, 1H), 1.30 (s, 3H), 1.26 (d, 3H), 1.18 (d, 3H), 1.14 (d, 3H), 1.06 (d, 3H), 0.92 (t, 3H).

TLC: DCM/MeOH 95/5 (Rf=0.57).

Intermediate 36

11S,21R)-3-Decladinosyl-11,12dideoy-6-methyl-3-oxo-12,11-[oxycarbonyl-(cyano-methylene]-erythromycin A A solution of intermediate 35 (0.024 g) in MeOH (1 mL) was stirred at room temperature for 24 h. Solvent evaporation under reduced pressure gave the title compound (0.020 g).

$^1$H-NMR (CDCl$_3$) δ: 5.26 (dd, 1H), 4.61 (d, 1H), 4.34 (d, 1H), 4.28 (m, 1H), 3.87 (q, 1H), 3.57 (m, 1H), 3.18 (m, 1H), 3.15 (t, 1H), 3.12 (m, 1H), 3.06 (m, 1H), 2.78 (s, —OCH$_3$), 2.62 (m, 1H), 2.46 (m, 1H), 2.27 (s, N(CH$_3$)$_2$), 1.91 (m, 1H), 1.84 (m, 1H), 1.70 (m, 1H), 1.68 (m, 1H), 1.62 (m, 1H), 1.57 (s, 3H), 1.41 (d, 3H), 1.34 (d, 3H), 1.34 (s, 3H), 1.24 (s, 1H), 1.26 (d, 3H), 1.14 (d, 3H), 1.07 (d, 3H), 0.92 (t, 3H).

TLC: DCM/MeOH 9/1 (Rf=0.38).

Intermediate 37

(10R,S,11R)-3-Decladinosyl-11,12-dideoxy-6-O-methyl-3-oxo-12,11-[oxycarbonylmethylene]-erythromycin A To a solution of intermediate 17 (0.050 g) in anhydrous DCM (25 mL), EDC (0.102 g) and DMSO (0.115 mL) were added under nitrogen atmosphere. The mixture was cooled to 0° C. and a solution of pyridinium trifluoroacetate (0.102 g) in DCM (0.5 mL) was added dropwise. The mixture was allowed to reach room temperature, after stirring for 5 h water (10 mL) was added and the mixture extracted with DCM (2×20 mL). The organic phase was dried over Na$_2$SO$_4$ and concentrated under reduced pressure The crude material was purified by preparative TLC (eluting with: DCM/MeOH 95/5); the recovered silica gel was stirred 18 h in MeOH then filtered. Solvent evaporation under reduced pressure gave the title compound (0.025 g).

$^1$H-NMR (CDCl$_3$) δ: 4.90 (dd, 1H), 4.32 (d, 1H), 4.24 (d, 1H), 3.85 (q, 1H), 3.56 (m, 1H), 3.32 (d, 1H), 3.18 (m, 1H), 3,12 (m, 1H), 3.02 (m, 1H), 2.80 (d, 1H), 2.71 (dd, 1H), 2.63 (s, —OCH$_3$), 2.55 (m, 1H), 2.47 (m, 1H), 2.27 (s, N(CH$_3$)$_2$), 1.87 (m, 1H), 1.70 (m, 1H), 1.62 (m, 1H), 1.58 (m, 1H), 1.50 (s, 3H), 1.38 (d, 3H), 1.30 (d, 3H), 1.31 (s, 3H), 1.30 (m, 1H), 1.25 (d, 3H), 1.22 (m, 1H), 1.14 (d, 3H), 1.07 (d, 3H), 0.86 (t, 3H).

Intermediate 38

(11S,21R,S)-2'-acetoxy-3-decladinosyl-11,12-dideoxy-6-O-allyl-3-oxo-12,11-[oxycarbonyl-(amino)-methylene]-erythromycin A A solution of intermediate 22 (0.52 g) in acetonitrile (66 mL) and a 1.2N HCl aqueous solution (154 mL) was stirred at room temperature for 1 h. After neutralising the mixture with solid Na₂CO₃ and evaporating the solvent under vacuum, the mixture was extracted with DCM (2×100 mL). The organic layer was dried over Na₂SO₄ and concentrated under reduced pressure to give of the title compound (0.47 g).

¹H-NMR (CDCl₃) δ: 5.88 (dd, 1H), 5.70 (m, 1H), 5.13 (d, 1H), 4.75 (m, 1H), 4.57 (s, 1H), 4.44 (d, 1H), 4.38 (d, 1H), 3.91 (q, 1H), 3.75 (q, dd), 3.61 (m, 1H), 3.50 (m, 1H), 3.24 (m, 1H), 3.08 (m, 1H), 2.70 (m, 1H), 2.64 (m, 1H), 2.46 (bs, 1H), 2.26 (s, N(CH₃)₂), 2.18 (m, 6H), 1.60–1.4 (m, 5H), 1.40–1.2 (m, 13H), 1.15 (d, 3H), 1.08 (d, 3H), 0.88 (t, 3H).

Intermediate 39

(11S,21R,S)-3-Decladinosyl-11,12-dideoxy-6-O-allyl-3-oxo-12,11-[oxycarbonyl-(amino)-methylene]-erythromycin A A solution of intermediate 38 (0.002 g) in MeOH (0.3 mL) was stirred at room temperature overnight. Solvent evaporation under reduced pressure gave the title compound (0.002 g).

¹H-NMR (CDCl₃) δ: 5.82 (dd, 1H), 5.73 (m, 1H), 5.14 (d, 1H), 5.02 (d, 1H), 4.54 (s, 1H), 4.40 (d, 1H), 4.38 (d, 1H), 3.93 (q, 1H), 3.76 (m, 1H), 3.62 (m, 1H), 3.52 (m, 1H), 3.24 (m, 1H), 3.21 (m, 1H), 3.09 (m, 1H), 2.66 (m, 1H), 2.50 (m, 1H), 2.47 (m, 1H), 2.28 (s, N(CH₃)₂), 1.95 (m, 1H), 1.85 (m, 2H), 1.80–0.80 (several m, 27H).

m\z ([MH]⁺)=653.

Intermediate 40

(11S,21R,S)-2'-O-Acetyl-3-decladinosyl-11,12-dideoxy-6-O-methyl-3-oxo-12,11-[oxycarbonyl-(amino)-methylene]-erythromycin A A solution of intermediate 29 (1.1 g) in acetonitrile (30 mL) and a 1.2N HCl aqueous solution (70 mL) was stirred at room temperature for 1 h. After neutralising the mixture with solid Na₂CO₃ and evaporating the solvent, the mixture was extracted with DCM (3×200 mL). The organic layer was dried over Na₂SO₄ and concentrated under vacuum to give the title compound (0.9 g).

¹H-NMR (CDCl₃) δ: 5.45 (dd, 1H), 4.75 (m, 1H), 4.45 (d, 1H), 4.40 (d, 1H), 4.21 (d, 1H), 3.82 (q, 1H), 3.54 (m, 1H), 3.09 (m, 1H), 2.69 (m, 1H), 2.68 (s, —OCH₃), 2.58 (m, 1H), 2.41(m, 1H), 2.25 (s, N(CH₃)₂), 2.07 (m, 3H), 1.95 (m, 1H), 1.75 (m, 1H), 1.60 (m, 1H), 1.49 (s, 3H), 1.39 (d, 3H), 1.35 (m, 1H), 1.31 (s, 3H), 1.26 (d, 3H), 1.17 (d+d, 6H), 1.09 (d, 3H), 0.88 (t, 3H).

TLC: DCM/MeOH 10/1 (Rf=0.48).

Intermediate 41

(11S,21R,S)-3-Decladinosyl-11,12-dideoxy-6-O-methyl-3-oxo-12,11-[oxycarbonyl-(amino)-methylene]-erythromycin A A solution of intermediate 40 (0.012 g) in MeOH (1 mL) was stirred at room temperature overnight. After evaporating the solvent, the crude material was purified by flash chromatography (eluting with: DCM/MeOH 100:5) to give the title compound (0.007 g).

¹H-NMR (CDCl₃) δ: 5.41 (dd, 1H), 4.42 (d, 1H), 4.33 (d, 1H), 4.22 (d, 1H),3.83 (q, 1H), 3.56 (m, 1H), 3.23 (d, 1H), 3.12 (m, 1H), 3.02 (m, 1H), 2.80 (d, 1H), 2.69 (s, —OCH₃), 2.60 (m, 1H), 2.54 (m, 1H), 2.40 (m, 1H), 2.33 (s, N(CH₃)₂), 1.95 (m, 3H), 1.9–1.50 (m, 3H), 1.49 (s, 3H), 1.39 (d, 3H), 1.35 (m, 1H), 1.33 (s, 3H), 1.32 (m, 1H), 1.31 (d, 3H), 1.26 (d, 3H), 1.16 (d, 3H), 1.10 (d, 3H), 0.88 (t, 3H).

EXAMPLE 1

(11S,21R)2'-O-Acetyl-3-decladinosyl-11,12-dideoxy-6-O-[(quinolin-3-yl)-propen-3-yl]-3-oxo-12,11-[oxycarbonyl-(cyano)-methylene]-erythromycin A A mixture of intermediate 33 0.065 g), palladium (II) acetate (0.004 g) and tri-o-tolylphosphine (0.011 g) in anhydrous DMF (2 mL) was flushed with nitrogen. To this solution 3-bromoquinoline (0.025 mL) and TEA (0.0026 mL) were added. The reaction mixture was heated at 50° C. for 30 min and stirred at 90° C. for 19 h. The reaction mixture was diluted with EtOAc (10 mL), washed with a 5% NaHCO₃ aqueous solution (10 mL) and brine (10 mL). The organic phase was dried over Na₂SO₄ and concentrated under reduced pressure. Purification of the crude material by flash chromatography (eluting with: DCM/MeOH/NH₃ 9.6/0.3/0.09) gave the title compound (0.010 g).

¹H-NMR (CDCl₃) δ: 8.99 (d, 1H), 8.14 (d, 1H), 8.08 (d, 1H), 7.85 (d, 1H), 7.66 (m, 1H), 7.53 (m, 1H), 6.58 (d, 1H), 6.27 (m, 1H), 5.47 (dd, 1H), 4.77 (d, 1H), 4.78 (m, 1H), 4.28 (d, 1H), 3.99 (m, 2H), 3.95 (q, 1H), 3.50 (m, 1H), 3.29 (s, 1H), 3.28 (m, 1H), 3.14 (m, 1H), 2.67 (m, 2H), 2.28 (s, N(CH₃)₂), 2.09 (s, 3H), 1.97 (m, 1H), 1.77–1.70 (m, 3H), 1.69 (m, 1H), 1.62 (s, 3H), 1.42 (s, 3H), 1.38 (d, 3H), 1.30 (m, 1H), 1.29 (d, 3H), 1.17 (d, 3H), 1.08 (d, 3H), 1.04 (d, 3H), 0.95 (t, 3H).

EXAMPLE 2

(11S,21R)-3-Decladinosyl-11,12-dideoxy-6-O-[(quinolin-3-yl)-propen-3-yl]-3-oxo-12,11-[oxycarbonyl-(cyano)methylene]-erythromycin A A solution of example 1 (0.010 g) in MeOH (1 mL) was stirred at room temperature overnight. Solvent evaporation under reduced pressure gave the title compound (0.007 g).

¹H-NMR (CDCl₃) δ: 9.00 (d, 1H), 8.15 (d, 1H), 8.07 (d, 1H), 7.84 (d, 1H), 7.65 (t, 1H), 7.52 (t, 1H), 6.58 (m, 1H), 6.29 (m, 1H), 5.45 (dd, 1H), 4.76 (d, 1H), 4.45 (d, 1H), 4.39 (d, 1H), 3.99 (m, 3H), 3.51 (m, 1H), 3.28 (s, 1H), 3.26 (m, 1H), 3.16 (m, 1H), 2.70 (m, 2H), 2.36 (m, 1H), 2.36 (s, N(CH₃)₂), 1.95 (m, 1H), 1.90–1.50 (m+s, 4H+3H), 1.43(s, 3H), 1.42 (d, 3H), 1.38 (s, 3H), 1.30 (m, 1H), 1.16 (d, 3H), 1.09 (d+d, 3H+3H), 0.94 (t, 3H).

EXAMPLE 3

(11S)-3-Decladinosyl-11,12-dideoxy-6-O-[(quinolin-3-yl)-propen-3-yl]-3-oxo-12,11-[oxycarbonyl-methylene]-erythromycin A A suspension of example 1 (0.020 g) and neutral activated aluminum oxide (0.030 g) in a mixture of THF/water 97/3 (3 mL) was heated under reflux for 4 days. The mixture was filtered and the solid residue washed with AcOEt (3×2 mL). The filtrate was dried over Na₂SO₄ and evaporated under reduced pressure. The crude material was dissolved in MeOH (1 mL) and stirred overnight. After evaporating the solvent, purification by flash chromatography (eluting with: DCM/MeOH 95:5) afforded the title compound (0.014 g).

¹H-NMR (CDCl₃) δ: 9.05 (d, 1H), 8.16 (d, 1H), 8.07 (d, 1H), 7.83 (d, 1H), 7.66 (t, 1H), 7.53 (t, 1H), 6.53 (d, 1H), 6.20 (m, 1H), 4.82 (dd, 1H), 4.44 (d, 1H), 4.38 (d, 1H), 4.00

(q, 1H), 3.86–3.68 (m, 2H), 3.60 (m, 1H), 3.28 (s, 1H), 3.19 (m, 1H), 3.15 (m, 1H), 3.10 (m, 1H), 2.84 (m, 1H), 2.64 (m, 1H), 2.44 (m, 1H), 2.38 (dd, 1H), 2.27 (s, N(CH$_3$)$_2$), 1.90–1.80 (m, 2H), 1.70 (m, 1H), 1.68 (m, 1H), 1.60 (m, 1H), 1.44 (s, 3H), 1.45 (d, 3H), 1.40 (d, 3H), 1.26 (s, 3H), 1.25 (m, 1H), 1.22 (d, 3H), 1.16 (d, 3H), 1.04 (d, 3H), 0.83 (t, 3H).

EXAMPLE 4

(11S,21R)3-Decladinosyl-11,12-dideoxy-6-O-[(quinolin-5-yl)-propen-3-yl]-3oxo-12,11-[oxycarbonyl-(cyano)-methylene]-erythromycin A A mixture of intermediate 33 (0.150 g), palladium (II) acetate (0.019 g) and tri-o-tolylphosphine (0.051 g) in anhydrous DMF (2 mL) was flushed with nitrogen. To this solution TEA (0.120 mL) and intermediate 30 (0.233 g) were added. The reaction mixture was stirred at 90° C. for 48 h. The reaction mixture was diluted with EtOAc (10 mL), the organic phase washed with a 5% NaHCO$_3$ aqueous solution (5 mL) and brine (5 mL), dried over Na$_2$SO$_4$ and concentrated under reduced pressure. The purification of the crude material by flash chromatography (eluting with: DCM/MeOH from 100/0 to 96/4) gave a compound that was dissolved in MeOH (3 mL) and stirred overnight at room temperature. After evaporation of the solvent, the crude material was purified by flash chromatography (eluting with: DCM/MeOH 94/6) affording the title compound (0.010 g).

$^1$H-NMR (CDCl$_3$) δ: 8.91 (m, 1H), 8.51 (d, 1H), 8.02 (d, 1H), 7.76 (d, 1H), 7.72 (t, 1H), 7.42 (m, 1H), 7.11 (d, 1H), 6.16 (m, 1H), 4.77 (d, 1H), 4.04 (d, 2H), 3.31 (m, 1H), 2.72 (m, 1H), 1.86 (m, 1H), 1.75 (m, 1H), 1.63 (s, 3H), 1.47 (s, 3H).

EXAMPLE 5

(11S,21R)-3-Decladinosyl-11,12dideoxy-6-O-[(quinolin-6-yl)-propen-3-yl]-3-oxo12,11-[oxycarbonyl-(cyano)-methylene]-erythromycin A A mixture of intermediate 33 (0.150 g), palladium (II) acetate (0.019 g) and tri-o-tolylphosphine (0.051 g) in anhydrous DMF (2 mL) was flushed with nitrogen. To this solution TEA (0.120 mL) and intermediate 31 (0.210 g) were added. The reaction mixture was heated at 90° C. for 24 h. The reaction mixture was diluted with EtOAc (10 mL), washed with a 5% NaHCO$_3$ aqueous solution (5 mL) and brine (5 mL), dried over Na$_2$SO$_4$ and concentrated under reduced pressure. The purification of the crude material by flash chromatography (eluting with: DCM/MeOH from 100/0 to 96/4) gave a compound that was dissolved in MeOH (3 mL) and stirred overnight at room temperature. After evaporation of the solvent, the crude material was purified by flash chromatography (eluting with: DCM/MeOH from 98/2 to 96/4) to give the title compound (0.015 g).

$^1$H-NMR (CDCl$_3$) δ: 8.85 (m, 1H), 8.15 (d, 1H), 8.06 (d, 1H), 7.89 (d, 1H), 7.74 (d, 1H), 7.37 (m, 1H), 6.59 (d, 1H), 6.21 (m, 1H), 4.76 (d, 1H), 3.99 (m, 2H), 3.30 (d, 1H), 3.16 (m, 1H), 2.70 (m, 1H), 1.85 (m, 1H), 1.73 (m, 1H), 1.63 (s, 3H), 1.44 (s, 3H).

EXAMPLE 6

(11S,21R)-3-Decladinosyl-11,12-dideoxy-6-O-[(quinolin-7-yl)-propen-3-yl]-3-oxo-12,11-[oxycarbonyl-(cyano)-methylene]-erythromycin A A mixture of intermediate 33 (0.200 g), palladium (II) acetate (0.025 g) and tri-o-tolylphosphine (0.068 g) in anhydrous DMF (3 mL) was flushed with nitrogen. To this solution TEA (0.160 mL) and intermediate 32 (0.310 g) were added. The reaction mixture was heated at 90° C. for 24 h. The reaction mixture was diluted with EtOAc (15 mL), washed with a 5% NaHCO$_3$ aqueous solution (10 mL) and brine (10 mL), dried over Na$_2$SO$_4$ and concentrated under reduced pressure. The purification of the crude material by flash chromatography (eluting with: DCM/MeOH from 100/0 to 96/4) gave a compound that was dissolved in MeOH (5 mL) and stirred overnight at room temperature. After solvent evaporation, the crude material was purified by flash chromatography (eluting with: DCM/MeOH from 100/0 to 90/10) to give the title compound (0.006 g).

$^1$H-NMR (CDCl$_3$) δ: 8.88 (m, 1H), 8.11 (d, 1H), 7.98 (s, 1H), 7.79 (s, 1H), 7.33 (m, 1H), 6.62 (d, 1H), 6.27 (m, 1H), 4.78 (m, 1H), 3.98 (m, 2H), 2.70 (m, 1H), 1.84 (m, 1H), 1.70 (m, 1H), 1.63 (s, 3H), 1.44 (s, 3H).

EXAMPLE 7

(11S,21R)-3-decladinosyl-11,12-dideoxy-6-O-[(quinolin-7-yl)-propyl]-3-oxo-12,11-[oxycarbonyl-(cyano)-methylene]-erythromycin A To a solution of example 2 (0.015 g) in MeOH (1.5 mL), palladium (10 wt. % on carbon powder, 0.015 g) was added and the mixture stirred under hydrogen atmosphere overnight. Filtration of the catalyst through a celite pad eluting with DCM (5 mL) and MeOH (5 mL) then purification by flash chromatography (eluting with: DCM/MeOH 96/4) gave the title compound (0.007 g).

$^1$H-NMR (CDCl$_3$) δ: 8.80 (m, 1H), 8.06 (d, 1H), 8.02 (d, 1H), 7.80 (d, 1H), 7.64 (t, 1H), 7.54 (t, 1H), 4.78 (m, 1H), 3.28 (m, 3H), 2.71 (m, 2H), 1.85 (m, 1H), 1.65 (m, 1H), 1.63 (s, 3H), 1.30 (s, 3H).

EXAMPLE 8

(11S,21R)-3-decladinosyl-11,12-dideoxy-6-O-[(quinolin-5-yl)-propen-3-yl]-3-oxo-12,11-[oxycarbonylmethylene]-erythromycin A To a solution of example 4 (0.010 g) in a mixture of THF/water 97/3 (2 mL) neutral activated aluminum oxide (0.040 g) was added and the reaction mixture stirred at 65° C. for 10 days. The mixture was filtered and the solid residue washed with EtOAc (3×5 mL) and DCM (3×5 mL). Solvent evaporation gave a crude material that was purified by flash chromatography (eluting with: DCM/MeOH from 100/0 to 98/2) to give the title compound (0.0015 g).

$^1$H-NMR (CDCl$_3$) δ: 8.92 (dd, 1H), 8.61 (d, 1H), 8.04 (d, 1H), 7.80 (d, 1H), 7.73 (dd, 1H), 7.43 (dd, 1H), 7.11 (d, 1H), 6.05 (m, 1H), 3.96–3.65 (m, 2H), 2.86 (m, 1H), 2.26 (m, 1H), 1.52 (s, 3H), 1.45 (s, 3H).

EXAMPLE 9

(11S,21R)-3-decladinosyl-11,12-dideoxy-6-O-[(quinolin-6-yl)-propen-3-yl]-3-oxo-12,11-[oxycarbonylmethylene]-erythromycin A To a solution of example 5 (0.010 g) in a mixture of THF/water 97/3 (2 mL) neutral activated aluminum oxide (0.040 g) was added and the reaction mixture stirred at 65° C. for 13 days. The mixture was filtered, the solid residue washed with EtOAc (3×10 mL) and DCM (3×10 mL). Solvent evaporation gave a crude material that was purified by flash chromatography (eluting with : DCM/MeOH from 100/0 to 95/5) to give the title compound (0.0015 g).

$^1$H-NMR (CDCl$_3$) δ: 8.92 (dd, 1H), 8.61 (d, 1H), 8.04 (d, 1H), 7.80 (d, 1H), 7.73 (dd, 1H), 7.43 (dd, 1H), 7.11 (d, 1H), 6.05 (m, 1H), 3.96–3.65 (m, 2H), 2.86 (m, 1H), 2.26 (m, 1H), 1.53 (s, 3H), 1.42 (s, 3H).

Pharmacy Examples

Tablets

|  | mg/tab |
| --- | --- |
| Active ingredient | 320 |
| Lactose | 150 |
| Ethyl cellulose | 20 |
| Sodium lauryl sulphate | 7 |
| Magnesium stearate | 3 |
| Tablet core | 500 |

The active ingredient and the lactose are blended together and then granulated using water as granulating fluid. The dried granules are blended with ethyl cellulose, sodium lauryl sulphate and magnesium stearate and the tablet core formed using an appropriate punch. The tablet may be coated using conventional technique and coatings.

Injection

The sterile vials were filled with the sterile active ingredient (500 mg). Purge the vial head space with sterile nitrogen; close the vials using rubber and metal overseals. The product may be constituted by dissolving in water for injection(10 ml) or other suitable sterile vehicle for injection shortly before administration.

Activity Data

The value of MIC (microbial inhibition concentration), obtained according to NCCLS (National Committee for Clinical Laboratory Standards), of the preferred compounds of the invention against erythromycin susceptible *Streptococcus pneumoniae* and *Streptococcus pyogenes* are less than or equal to 0.06 ug/ml.

In particular examples 2, 3, 5 and 6 showed MIC in the range 0.1–64 ug/ml against erythromycin resistant *Streptococcus pneumoniae* strains.

What is claimed is:

1. A compound of formula (I)

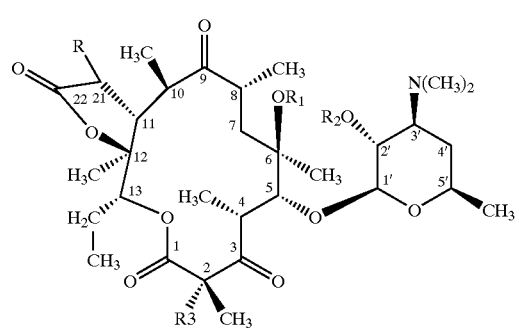

(I)

wherein

R is hydrogen, cyano or NR$_4$R$_5$;

R$_1$ is XR$_6$;

R$_2$ is hydrogen or a hydroxyl protecting group;

R$_3$ is hydrogen or halogen;

R$_6$ is selected from:

(i) unsubstituted phenyl or phenyl substituted by 1 to 2 groups, which may be the same or different, selected from (CH$_2$)$_r$R$_7$ wherein r is zero or an integer from 1 to 4 and R$_7$ is selected from: hydrogen;
halogen;
C$_{1-4}$ alkoxy;
hydroxy;
cyano;
nitro;
trifluoromethyl;
carboxy;
NR$_4$R$_5$;
CONR$_4$R$_5$;
NHCOR$_8$;
NR$_5$CONR$_8$R$_5$;
NHS(O$_2$)R$_9$;
S(O)$_n$R$_8$;
C$_{1-4}$ alkanoyl amino,
phenyl optionally substituted by halogen, C$_{1-4}$ alkoxy or NR$_4$R$_5$;
phenoxy;
a 5-membered heteroaryl containing at least 1 heteroatom selected from oxygen, sulphur and nitrogen; and
a 6-membered heteroaryl group containing at least 1 nitrogen atom;

wherein n is 0 or an integer from 1 to 2;

R$_4$ is hydrogen, C$_{1-4}$ alkyl or C(O)R$_5$,

R$_5$ is hydrogen or C$_{1-4}$ alkyl,

R$_8$ is C$_{1-4}$alkyl, phenyl, a 5 membered heteroaryl containing at least 1 heteroatom selected from oxygen, sulphur and nitrogen, or a 6-membered heteroaryl group containing at least 1 nitrogen atom, and R$_9$ is C$_{1-4}$ alkyl or phenyl;

(ii) a 5 or 6 membered heteroaryl in which the 5-membered heteroaryl contains at least one heteroatom selected from oxygen, sulphur and nitrogen and the 6-membered heteroaryl group contains from 1 to 3 nitrogen atoms, wherein the 5 or 6 membered heteroaryl is unsubstituted or is substituted by 1 or 2 groups, which may be the same or different, selected from (CH$_2$)$_{rR7}$, wherein r is zero or an integer from 1 to 4 and R$_7$ is selected from:
hydrogen;
halogen;
C$_{1-4}$ alkoxy;
hydroxy;
cyano;
nitro;
trifluoromethyl;
carboxy;
NR$_4$R$_5$;
CONR$_4$R$_5$;
NHCOR$_8$;
NR$_5$CONR$_8$R$_5$;
NHS(O$_2$)R$_9$;
S(O)$_n$R$_8$;
C$_{1-4}$ alkanoyl amino;
phenyl optionally substituted by halogen, C$_{1-4}$ alkoxy or NR$_4$R$_5$;
phenoxy;
a 5-membered heteroaryl containing at least 1 heteroatom selected from oxygen, sulphur and nitrogen; and
a 6-membered heteroaryl group containing at least 1 nitrogen atom;

wherein n, $R_4$, $R_5$, $R_8$ and $R_9$ are as defined above;
  (iii) a 5–6 membered heterocyclic group containing at least 1 heteroatom selected from oxygen, sulphur and nitrogen;
  (iv) a 9 to 10 membered fused bicyclic carbocyclic ring, which can be a 5,6/6,5 or 6,6 bicyclic ring system which is saturated, unsaturated or aromatic, containing at least one heteroatom selected from oxygen, sulphur and nitrogen;
or
  (v) a 9 or 10 membered fused bicyclic heterocyclic group, which can be a 5,6/6,5 or 6,6 bicyclic ring system which is saturated, unsaturated or aromatic, containing at least one heteroatom selected from oxygen, sulphur and nitrogen, wherein the 9 or 10 membered fused bicyclic heterocyclic group is unsubstituted or is substituted by one to 2 substituents which may be the same or different and are selected from alkyl, halogen, cyano, nitro, trifluoromethyl and $NR_4R_5$, wherein $R_4$ and $R_5$ have the meanings as defined above;
X is a $C_{1-10}$ alkylene, a $C_{3-10}$ alkenylene or a $C_{3-10}$ alkynylene chain wherein said chains are:
  i) optionally interrupted by a bivalent radical group selected from —$N(R_5)$—, —C(O)—, —$S(O)n$—, —$N(R_5)C(O)$—, and —$C(O)N(R_5)$—,
  ii) optionally substituted by one or two groups selected from:
    $C_{1-4}$ alkyl, oxo, $C_{1-4}$ alkoxy, halogen, cyano, phenoxy, hydroxy, and $NR_4R_5$;
wherein n, $R_4$ and $R_5$ have the meanings as defined above; and a pharmaceutically acceptable salt or solvate thereof.

2. A compound as claimed in claim 1 wherein $R_2$ is hydrogen.

3. A compound as claimed in claim 1 wherein $R_3$ is hydrogen or fluorine.

4. A compound as claimed in claim 1, wherein $R_6$ is a group selected from phenyl, quinolinyl, pyridinyl-imidazolyl and pyridinyl-4-thiazolyl.

5. A compound as claimed in claim 1, wherein X is a $C_{1-6}$ alkylene or $C_{3-6}$ alkenylene chain, $R_6$ is a group selected from phenyl, quinolinyl, pyridyl-imidazolyl, and pyridyl-4-thiazolyl, and $R_2$, $R_3$, $R_4$ and $R_5$ are hydrogen.

6. A compound selected from:
  (11S,21R)-3-Decladinosyl-11,12-dideoxy-6-O-[(quinolin-3-yl)-propen-3-yl]-3-oxo-12,11-[oxycarbonyl-(cyano)-methylene]-erythromycin A;
  (11S)-3-Decladinosyl-11,12-dideoxy-6-O-[(quinolin-3-yl)propen-3-yl]-3-oxo-12,11-[oxycarbonyl-methylene]-erythromycin A;
  (11S,21R)-3-Decladinosyl-11,12-dideoxy-6-O-[(quinolin-5-yl)-propen-3-yl]-3-oxo-12,11-[oxycarbonyl-(cyano)-methylene]-erythromycin A;
  (11S,21R)-3-Decladinosyl-11,12-dideoxy-6-O-[(quinolin-6-yl)-propen-3-yl]-3-oxo-12,11-[oxycarbonyl-(cyano)-methylene]-erythromycin A; and
  (11S,21R)-3-Decladinosyl-11,12-dideoxy-6-O-[(quinolin-7-yl)-propen-3-yl]-3-oxo-12,11-[oxycarbonyl-(cyano)methylene]-erythromycin A.

7. A process for the preparation of a compound as claimed in claim 1, which process comprises one of:
  a) cyclizing a compound of formula (IV) in the presence of potassium cyanide, wherein $R_{1a}$ has the meaning defined in claim 1 for $R_1$ or is a group convertible thereto, $R_2$ and $R_3$ have the meanings defined in claim 1, $R_{10}$ is a cladinose derivative of formula (III) or hydroxy, and $R_{11}$ is hydrogen, $R_{11}$ together with $R_{10}$ and the carbon atom to which they are attached are C=O,

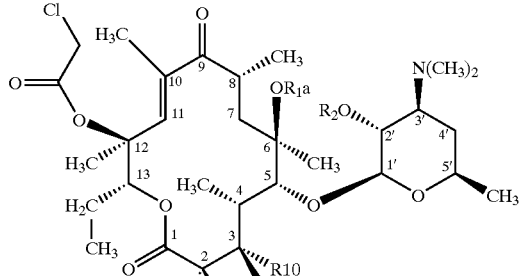

(IV)

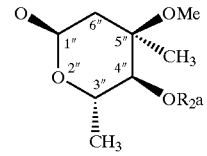

(III)

and optionally subjecting the resulting compound to one or more of the following operations:
  i) conversion of the group $R_{1a}$ into the group $R_1$; ii) hydrolysis of the cladinose derivative (III);
  iii) conversion of the 3-hydroxy group into the 3-oxo; iv) removal of the protecting group $R_2$;
  and v) conversion of the resultant compound of formula(I) into a pharmaceutically acceptable salt or solvate thereof
to produce a compound of formula (I) wherein R is cyano;
or
  b) eliminating the cyano group from a compound of formula (IVa) by treatment of a compound of formula (IVa) with aluminum oxide, wherein $R_{1a}$, $R_{10}$ and $R_{11}$ have the meanings defined for compounds of formula (IV), and $R_2$ and $R_3$ have the meanings defined in claim 1,

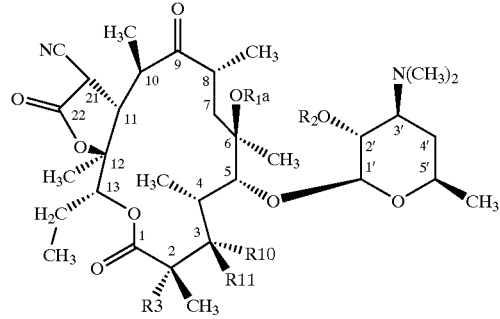

IVa and optionally subjecting the resulting compound to one or more of the following operations:
  i) conversion of the group $R_{1a}$ into the group $R_1$; ii) hydrolysis of the cladinose derivative (III); iii) conversion of the 3-hydroxy group into 3-oxo; iv) removal of the protecting group $R_2$; and v) conversion of the resultant compound of formula(I) into a pharmaceutically accentable salt or solvate thereof to produce a compound of formula (I) wherein R is hydrogen; or c) reacting an amino compound of formula (V) wherein $R_{1a}$, $R_{10}$, and $R_{11}$ have the meanings defined for compounds of formula (IV), and $R_2$ and $R_3$ have the meanings defined in claim 1,

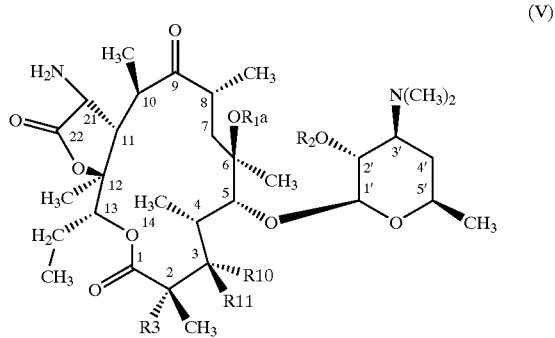

(V)

with a suitable alkylating agent of formula L-$R_4$ (VI), wherein $R_4$ is $C_{1-4}$ alkyl and L is a suitable leaving group and optionally subjecting the resulting compound to one or more of the following operations:

i) conversion of the group $R_{1a}$ into the group $R_1$; ii) hydrolysis of the cladinose derivative (III);

iii) conversion of the 3-hydroxy group into 3-oxo; iv) removal of the protecting group $R_2$; and v) conversion of the resultant compound of formula(I) into a pharmaceutically acceptable salt or solvate thereof to produce a compound of formula(I) wherein $R_4$ is $C_{1-4}$ alkyl and $R_5$ is hydrogen or $C_{1-4}$ alkyl; or d) reacting an amino compound of formula (V) wherein $R_{1a}$, $R_{10}$ and $R_{11}$ have the meanings defined for compounds of formula (IV) $R_2$ and $R_3$ have the meanings defined in claim 1, with an activated derivative of the acid HO(O)C$R_5$ (VIa)

and optionally subjecting the resulting compound to one or more of the following operations:

i) conversion of the group $R_{1a}$ into the group $R_1$; ii) hydrolysis of the cladinose derivative (III);

iii) conversion of the 3-hydroxy group into 3-oxo; iv) removal of the protecting group $R_2$; and v) conversion of the resultant compound of formula (I) into a pharmaceutically acceptable salt or solvate thereof to produce a compound of formula (I) wherein R is $NR_4R_5$, $R_4$ is $C(O)R_5$; and $R_5$ is H; or e) cyclizing a compound of formula (VII) wherein $R_{12}$ is a suitable nitrogen protecting group, $R_2$ and $R_3$ have the meanings defined in claim 1, and $R_{1a}$, $R_{10}$ and $R_{11}$ have the meaning defined in formula (IV),

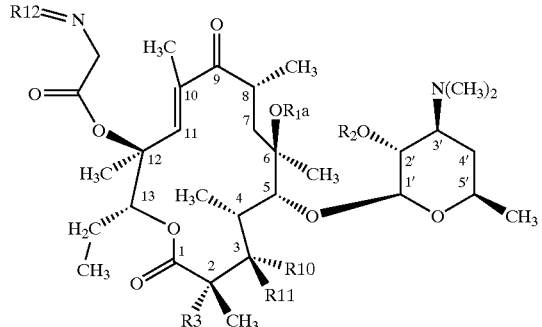

(VII)

in the presence of an organic base, followed by removal of the nitrogen protecting group, and optionally subjecting the resulting compound to one or more of the following operations:

i) conversion of the group $R_{1a}$ into the group $R_1$; ii) hydrolysis of the cladinose derivative (III);

iii) conversion of the 3-hydroxy group into 3-oxo; iv) removal of the protecting group $R_2$; and v) conversion of the resultant compound of formula (I) into a pharmaceutically accentable salt or solvate thereof to produce a compound of formula(I) wherein R is $NH_2$; or f) reacting a compound of formula (I), wherein $R_{1a}$, $R_{10}$ and $R_{11}$ have the meanings defined for compounds of formula (IV), $R_3$ is hydrogen, and $R_2$ is a hydroxy protecting group, with a halogenating agent and optionally subjecting the resulting compound to one or more of the following operations:

i) conversion of the group $R_{1a}$ into the group $R_1$; ii) hydrolysis of the cladinose derivative (III); iii) conversion of the 3-hydroxy group into 3-oxo; iv) removal of the protecting group $R_2$; and v) conversion of the resultant compound of formula (I) into a pharmaceutically acceptable salt or solvate thereof to produce a compound of formula (I) wherein $R_3$ is halogen.

8. A pharmaceutical composition comprising a compound as claimed in claim 1, in admixture with one or more pharmaceutically acceptable carriers or excipients.

9. A method for the treatment of a human or non human animal body to combat bacterial infection comprising administration of an effective amount of a compound as claimed in claim 1.

* * * * *